(12) United States Patent
Van Eis et al.

(10) Patent No.: US 7,648,989 B2
(45) Date of Patent: *Jan. 19, 2010

(54) INDOLYLMALEIMIDE DERIVATIVES AS PKC INHIBITORS

(75) Inventors: Maurice Van Eis, Buschwiller (FR); Peter Von Matt, Biel-Benken (CH); Jürgen Wagner, Bottmingen (CH); Jean-Pierre Evenou, St. Louis (FR); Walter Schuler, Grenzach-Wyhlen (DE)

(73) Assignee: Novartis AG, Basel (CH)

( * ) Notice: Subject to any disclaimer, the term of this patent is extended or adjusted under 35 U.S.C. 154(b) by 356 days.

This patent is subject to a terminal disclaimer.

(21) Appl. No.: 10/586,421

(22) PCT Filed: Jan. 19, 2005

(86) PCT No.: PCT/EP2005/000502

§ 371 (c)(1), (2), (4) Date: Oct. 18, 2006

(87) PCT Pub. No.: WO2005/068455

PCT Pub. Date: Jul. 28, 2005

(65) Prior Publication Data

US 2008/0242675 A1 Oct. 2, 2008

(30) Foreign Application Priority Data

Jan. 19, 2004 (GB) ................................. 0401089.8
Jan. 19, 2004 (GB) ................................. 0401090.6

(51) Int. Cl.
*A61K 31/497* (2006.01)
*A61K 31/4025* (2006.01)
*C07D 403/14* (2006.01)

(52) U.S. Cl. .................. 514/253.01; 514/422; 544/364; 548/466

(58) Field of Classification Search ................. 544/364; 548/466; 514/253.01, 422
See application file for complete search history.

(56) References Cited

U.S. PATENT DOCUMENTS

| 5,057,614 A | 10/1991 | Davis et al. |
| RE36,736 E | 6/2000 | Davis et al. |
| 7,220,774 B2 * | 5/2007 | Albert et al. ................. 514/414 |

FOREIGN PATENT DOCUMENTS

| WO | 02/38561 | 5/2002 |
| WO | WO02/38561 | 5/2002 |
| WO | WO03/082859 | 10/2003 |
| WO | WO03/103663 | 12/2003 |

OTHER PUBLICATIONS

Martiny-Baron et al., Selective Inhibition of Protein Kinase C Isozymes by the Indolocarbazole Gö 6976*, The Journal of Biological Chemistry, vol. 268, No. 13, pp. 9194-9197 (1993) USA.
British Search Report of GB0401090.6 dated May 19, 2004.

* cited by examiner

*Primary Examiner*—Kamal A Saeed
*Assistant Examiner*—Samantha L Shterengarts
(74) *Attorney, Agent, or Firm*—Hoxie & Associates LLC; Jay Pattumudi

(57) ABSTRACT

This invention relates to PKC inhibitors which are able to selectively inhibit e.g. the and optionally 0, isoforms of PKC, and their use in particular in transplantation.

5 Claims, No Drawings

INDOLYLMALEIMIDE DERIVATIVES AS PKC INHIBITORS

CROSS REFERENCE TO RELATED APPLICATIONS

This application is a U.S. filing under 35 U.S.C. 371 of PCT/EP2005/000502 filed on Jan. 19, 2005, which claims the benefit of both GB 0401089.8, filed on Jan. 19, 2004, and GB 0401090.6, filed on Jan. 19, 2004, the disclosures of each of which are incorporated herein by reference.

The present invention relates to new inhibitors of Protein Kinase C (PKC) which are selective over other protein kinases, new inhibitors of PKC which are selective for the isoforms α and β, and optionally θ, of the PKC, over one or more of the other existing PKC isoforms and the use of such PKC inhibitors to inhibit graft rejection or autoimmune diseases.

Protein Kinase C (PKC) consists of a family of closely related enzymes that function as serine/threonine kinases. At present there are at least ten known isoenzymes of PKC that differ in their tissue distribution, enzymatic selectivity, requirement for $Ca^{2+}$, and regulation. PKCs play an important role in cell-cell signaling, gene expression and in the control of cell differentiation and growth. A number of PKC inhibitors are already known. Some are also known to demonstrate selectivity for PKC over other protein kinases. However very little is known regarding isoenzyme selectivity. Because of the important roles in physiology of the different PKC isoenzymes there is a need to develop selective PKC inhibitors, in particular PKC inhibitors highly selective over the other protein kinases, and/or for certain specific isozymes of PKC.

Surprisingly compounds which are selective PKC inhibitors have now been identified, hereinafter referred to as compounds of the invention. Furthermore, it has been found that these selective PKC inhibitors show interesting therapeutic properties, in particular in transplantation and to treat or prevent autoimmune diseases.

In one aspect, the present invention provides a compound which is a protein-selective inhibitor of Protein Kinase C, e.g. an inhibitor selective for PKC over one or more other protein kinases, e.g. over one or more tyrosine kinases, for instance. over one or more non-receptor or receptor tyrosine kinases, e.g. over one or more of PKA, PKB, Abl Met, Src, Ins-R, Flt-3, JAK-2, KDR and/or Ret proteins. The selective PKC inhibitors of the invention may optionally be selective over one or more serine/threonine kinases, e.g. one or more serine/threonine kinases which do not belong to the CDK family. Preferably the compounds of the invention show a selectivity of at least 10 fold, more preferably 20 fold, most preferably 100 fold for the PKC over one or more other protein kinases, e.g. over one or more tyrosine kinases, e.g. over Flt-3, JAK-2, KDR and/or Ret proteins, or over one or more serine/threonine kinases which do not belong to the CDK family.

In one embodiment of the invention, there is provided a PKC inhibitor which is selective for PKC over the serine/threonine kinases which do not belong to the CDK-family, e.g. serine/threonine kinases which are not CDK-1 protein.

The selectivity of a selective inhibitor of PKC over other protein kinases may be calculated as the ratio of the $IC_{50}$ measured for PKC in the assay described below over the $IC_{50}$ determined for another kinase In another embodiment of the invention, there is provided a PKC inhibitor for which the ratio of the $IC_{50}$ value as determined in an Allogeneic Mixed Lymphocyte Reaction (MLR) assay to the $IC_{50}$ value as determined in a BM assay is higher than 5, 10, 20 or 30, preferably higher than 20 or 30.

MLR and BM assays can be done according to known methods, e.g. mouse of human MLR and BM assays. preferably as disclosed hereinafter.

In another aspect, the present invention provides a selective inhibitor of Protein Kinase C (PKC), i.e. isozyme-selective PKC inhibitors, wherein the compound possesses selectivity for the isoforms α and β of the PKC, over one or more of the other PKC isoforms.

Preferably the compounds of the invention are selective for the α and β PKCs over one or more of the other PKC isoforms, e.g. over one or more PKC isoforms selected from δ, ε, η and θ, preferably over δ and ε PKC isoforms, more preferably over δ, ε and η PKC isoforms, and even more preferably over δ, ε, η and θ PKC isoforms.

In another embodiment of the invention, the compounds of the invention are selective for the α, β and θ PKCs over the one or more of the other PKC isoforms, e.g. over one or more PKC isoforms selected from δ, ε and η, preferably over δ and ε PKC isoforms, more preferably over δ, ε and η PKC isoforms.

The compounds of the invention preferably show a selectivity of at least 10 fold, more preferably 20 fold, most preferably 100 fold for the PKCs α and β, and optionally θ, over one or more of the other PKC isoforms, e.g. over one or more PKC isoforms selected from δ, ε, η and θ, preferably over the PKC isoform δ, more preferably over the PKC isoforms ε and η, and even more preferably over the PKC isoforms δ, ε and η.

Selectivity for the α, β or θ isoforms of the PKC over one or more of the other PKC isoforms can be measured by comparing the $IC_{50}$ of the compound for the α, β or θ PKC to the $IC_{50}$ of the compound for the other PKC isoforms, e.g. δ, ε, η. Preferably, the selectivity can be determined by calculating the ratio of $IC_{50}$ of the compound for the δ, ε or η PKC isoforms to the $IC_{50}$ of the compound for the α, β or θ PKC.

$IC_{50}$ values may be obtained, for example, according to the PKC assay described below.

In a preferred embodiment, the compounds of the invention show an $IC_{50}$ value for the α and β, and optionally θ, PKCs of 1 μM or less, preferably 10 nM or less in the hereinafter mentioned assay.

Preferably, the compounds of the invention show a selectivity over the α and β, and optionally θ, isoforms of PKC, as well as a selectivity over one or more of the other protein kinases, e.g. over one or more tyrosine kinases, or over one or more serine/threonine kinases which do not belong to the CDK-family, e.g. over one or more of PKA, PKB, Abl, Met, Src, Ins-R, Flt-3, JAK-2, KDR and Ret proteins, e.g. over one or more of Flt-3, JAK-2, KDR and Ret proteins.

The compounds of the invention in free form or in pharmaceutically acceptable salt form are useful in the treatment and/or prevention of diseases or disorders mediated by T lymphocytes and/or PKC, e.g. mediated by α and β, and optionally θ PKCs, e.g. acute or chronic rejection of organ, tissue or cells allo- or xenografts, graft versus host diseases, autoimmune diseases, inflammatory diseases, infectious diseases, cancer or cardiovascular diseases e.g. heart failure. The term "transplant" as well as "cells, tissue or organ" encompasses, for example, skin, eye or portions of the eye (e.g., cornea, retina, lens), bone marrow, muscle, heart, lung, heartlung, liver, kidney, pancreas (e.g., islet cells, β-cells), parathyroid, bowel (e.g., colon, small intestine, duodenum), neuronal tissue, bone and vasculature (e.g., artery, vein).

The selective PKC inhibitors of the invention are, therefore, useful in the treatment and/or prevention of atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock, e.g. traumatic brain injury. The isozyme selective PKC inhibitors of the invention are also useful in the treatment and/or prevention of T-cell mediated acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes type I or II and the disorders associated therewith, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis.

The selective PKC inhibitors of the invention in free form or in pharmaceutically acceptable salt form exhibit valuable pharmacological properties, e.g. as indicated by the following in vitro and in vivo tests.

A. In Vitro Tests

1. In vitro Determination of the Specificity and Selectivity of the PKC Inhibitors The compounds of the invention are tested for their activity on different PKC isoforms according to the following method. Assay is performed in a white with clear bottom 384-well microtiterplate with non-binding surface. The reaction mixture (25 µl) contains 1.5 µM of a tridecapeptide acceptor substrate that mimics the pseudo substrate sequence of PKC α with the Ala→Ser replacement, 10 µM $^{33}$P-ATP, 10 mM $Mg(NO_3)_2$, 0.2 mM $CaCl_2$, PKC at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 min at room temperature. Reaction is stopped by adding 50 µl of stop mix (100 mM EDTA, 200 µM ATP, 0.1% Triton X-100, 0.375 mg/well streptavidin-coated SPA beads in phosphate buffered saline w/o Ca, Mg. After 10 min incubation at room temperature, the suspension is spun down for 10 min at 300 g. Incorporated radioactivity is measured in a Trilux counter for 1 min. $IC_{50}$ measurement is performed on a routine basis by incubating a serial dilution of inhibitor at concentrations ranging between 1-1000 µM. $IC_{50}$ values are calculated from the graph by curve fitting with XL fit® software.

2. Protein Kinase Cα Assay

Human recombinant PKCα is obtained from Oxford Biomedical Research and is used under the assay conditions as described under Section A.1 above. In this assay, compounds of the invention, e.g. compounds of formula I, inhibit PKCα with an $IC_{50} \leq 1$ µM, preferably $\leq 10$ nM 3. Protein Kinase Cβ1 Assay Human recombinant PKCβ1 is obtained from Oxford Biomedical Research and is used under the assay conditions as described under Section A.1 above. In this assay, compounds of the invention, e.g. compounds of formula I, inhibit PKCβ1 with an $IC_{50} \leq 1$ µM, preferably $\leq 10$ nM 4. Protein Kinase Cδ Assay Human recombinant PKCδ is obtained from Oxford Biomedical Research and is used under the assay conditions as described under Section A.1 above. In this assay, compounds of the invention, e.g. compounds of formula I, inhibit PKCδ with an $IC_{50} \leq 1$ µM.

5. Protein Kinase Cε Assay

Human recombinant PKCε is obtained from Oxford Biomedical Research and is used under the assay conditions as described under Section A.1 above. In this assay, compounds of the invention, e.g. compounds of formula I, inhibit PKCε with an $IC_{50} \leq 1$ µM.

6. Protein Kinase Cη Assay

Human recombinant PKCη is obtained from PanVera and is used under the assay conditions as described under Section A.1 above. In this assay, compounds of the invention, e.g. compounds formula I, inhibit PKCη with an $IC_{50} \leq 1$ µM.

7. Protein Kinase Cθ Assay

Human recombinant PKCθ is used under the assay conditions as described above. In this assay, compounds of the invention, e.g. compounds of formula I, inhibit PKC θ with an $IC_{50} \leq 1$ µM.

8. CD28 Costimulation Assay

The assay is performed with Jurkat cells transfected with a human interleukin-2 promoter/reporter gene construct as described by Baumann G et al. in Transplant. Proc. 1992;24: 43-8, the β-galactosidase reporter gene being replaced by the luciferase gene (de Wet J., et al., Mol. Cell Biol. 1987, 7(2), 725-737). Cells are stimulated by solid phase-coupled antibodies or phorbol myristate acetate (PMA) and the $Ca^{++}$ ionophore ionomycin as follows. For antibody-mediated stimulation Microlite TM1 microtiter plates (Dynatech) are coated with 3 µg/ml goat anti-mouse IgG Fc antibodies (Jackson) in 55 µl phosphate-buffered saline (PBS) per well for three hours at RT. Plates are blocked after removing the antibodies by incubation with 2% bovine serum albumin (BSA) in PBS (300 µl per well) for 2 hours at RT. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% $CO_2$. 100 µl of this mixture containing $1 \times 10^5$ cells are then transferred to the antibody-coated assay plates. In parallel 100 µl are incubated with 40 ng/ml PMA and 2 µM ionomycin. After incubation for 5.5 hours at 37° C. in 5% $CO_2$, the level of luciferase is determined by bioluminescence measurement. The plates are centrifuged for 10 min at 500 g and the supernatant is removed by flicking. Lysis buffer containing 25 mM Tris-phosphate, pH 7.8, 2 mM DTT, 2 mM 1.2-diaminocyclohexane-N,N,N',N-tetraacetic acid, 10% (v/v) glycerol and 1% (v/v) Triton X-100 is added (20 µl per well). The plates are incubated at RT for 10 minutes under constant shaking. Luciferase activity is assessed with a bioluminescence reader (Labsystem, Helsinki, Finland) after automatic addition of 50 µl per well luciferase reaction buffer containing 20 mM Tricine, 1.07 mM $(MgCO_3)_4Mg(OH)_2 \times 5H_2O$, 2.67 mM $MgSO_4$, 0.1 mM EDTA, 33.3 mM DTT, 270 μM coenzyme A, 470 μM luciferin (Chemie Brunschwig AG), 530 μM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves. In this assay, compounds of formula I inhibit anti-T cell receptor/anti-CD28 and PMA/ionomycin stimulated Jurkat cells with an $IC_{50} \leq 1$ μM.

9. Bone Marrow Proliferative (BM) Assay

Bone marrow cells from CBA mice ($2.5 \times 10^4$ cells per well in flat bottom tissue culture microtiter plates) are incubated in 100 μl RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland), WEHI-3 conditioned medium (7.5% v/v) and L929 conditioned medium (3% v/v) as a source of growth factors and serially diluted compounds. Seven three-fold dilution steps in duplicates per test compound are performed. After four days of incubation 1 μCi $^3$H-thymidine is added. Cells are harvested after an additional five-hour incubation period, and incorporated $^3$H-thymidine is determined according to standard procedures. Conditioned media are prepared as follows. WEHI-3 cells (ATCC TIB68) and L929 cells (ATCC CCL 1) are grown in RPMI medium until confluence for 4 days and one week, respectively. Cells are harvested, resuspended in the same culture flasks in medium C containing 1% FCS (Schreier and Tees 1981) for WEHI-3 cells and RPMI medium for L929 cells and incubated for 2 days (WEHI-3) or one week (L929). The supernatant is collected, filtered through 0.2 μm and stored in aliquots at −80° C. Cultures without test compounds and without WEHI-3 and L929 supernatants are used as low control values. Low control values are subtracted from all values. High controls without any sample are taken as 100% proliferation. Percent inhibition by the samples is calculated and the concentrations required for 50% inhibition ($IC_{50}$ values) are determined.

10. Allogeneic Mixed Lymphocyte Reaction (MLR) Assay

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined. Preferably, compounds of the invention show an $IC_{50}$ value as determined by MLR assay lower than 100 μM, preferably lower than 10 μM, more preferably lower than 1 μM.

B. In Vivo

Rat Heart transplantation

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 10/0 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when heart beat stops. Increases of graft survival are obtained in animals treated with a compound of formula I administered orally at a daily dose of 1 to 150 mg/kg bid, preferably 1 to 30 mg/kg bid or 10 to 100 mg/kg bid.

Graft v. Host Model

Spleen cells ($2 \times 10^7$) from Wistar/F rats are injected subcutaneously into the right hind footpad of (Wistar/F×Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound.

Representative examples of compounds which are selective PKC inhibitors e.g. include indolylmaleimide derivatives of formula I

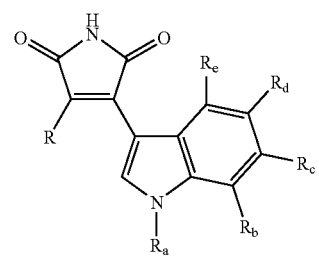

I wherein
$R_a$ is H; $C_{1-4}$alkyl; or $C_{1-4}$alkyl substituted by OH, $NH_2$, $NHC_{1-4}$alkyl or $N(di-C_{1-4}alkyl)_2$; one of $R_b$, $R_c$, $R_d$ and $R_e$ is halogen; $C_{1-4}$alkoxy; $C_{1-4}$alkyl; $CF_3$ or CN and the other three substituents are each H; or $R_b$, $R_c$, $R_d$ and $R_e$ are all H; and R is a radical of formula (a), (b) or (c)

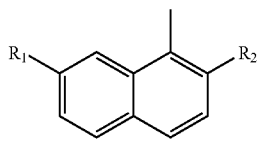

(a)

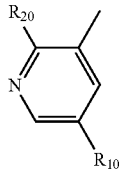

(b)

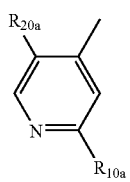

(c)

wherein
R$_1$ is —(CH$_2$)$_n$—NR$_3$R$_4$,
  wherein
    each of R$_3$ and R$_4$, independently, is H or C$_{1-4}$alkyl; or R$_3$ and R$_4$ form together with the nitrogen atom to which they are bound a heterocyclic residue;
    n is 0, 1 or 2; and
R$_2$ is H; halogen; C$_{1-4}$alkyl; CF$_3$; OH; SH; NH$_2$; C$_{1-4}$alkoxy; C$_{1-4}$alkylthio; NHC$_{1-4}$alkyl; N(di-C$_{1-4}$alkyl)$_2$, CN, alkyne or NO$_2$;
Each of R$_{10}$ and R$_{10a}$, independently, is a heterocyclic residue; or a radical of formula α

 —X—R$_f$—Y   (α)

wherein X is a direct bond, O, S or NR$_{11}$ wherein R$_{11}$ is H or C$_{1-4}$alkyl,
R$_f$ is C$_{1-4}$alkylene or C$_{1-4}$alkylene wherein one CH$_2$ is replaced by CR$_x$R$_y$ wherein one of R$_x$ and R$_y$ is H and the other is CH$_3$ each of R$_x$ and R$_y$ is CH$_3$ or R$_x$ and R$_y$ form together —CH$_2$—CH$_2$—,
Y is bound to the terminal carbon atom and is selected from OH, —NR$_{30}$R$_{40}$ wherein each of R$_{30}$ and R$_{40}$, independently, is H, C$_{3-6}$cycloalkyl, C$_{3-6}$cycloalkyl-C$_{1-4}$alkyl, aryl-C$_{1-4}$alkyl, heteroaryl-C$_{1-4}$alkyl, C$_{2-6}$alkenyl or C$_{1-4}$alkyl optionally substituted on the terminal carbon atom by OH, halogen, C$_{1-4}$alkoxy or —NR$_{50}$R$_{60}$ wherein each of R$_{50}$ and R$_{60}$, independently, is H, C$_{1-4}$alkyl, C$_{3-6}$cycloalkyl, C$_{3-6}$cycloalkyl-C$_{1-4}$alkyl, aryl-C$_{1-4}$alkyl, or R$_{30}$ and R$_{40}$ form together with the nitrogen atom to which they are bound a heterocyclic residue; and
each of R$_{20}$ and R$_{20a}$, independently, is H; halogen; C$_{1-4}$alkyl; C$_{1-4}$alkoxy; CF$_3$; nitrile; nitro or amino, in free form or in salt form.

The compounds of formula I are novel and therefore form also part of the invention.

Preferably Y comprises a nitrogen as heteroatom and optionally a second heteroatom, preferably selected from N, O and S, and optionally substituted.

It will be appreciated that the isozyme selective PKC inhibitors of the invention, e.g. compounds of formula I, may exist in the form of optical isomers, racemates or diastereoisomers. For example, a ring carbon atom bearing a substituent in the position 3 of the piperazinyl residue is asymmetric and may have the R- or S-configuration. It is to be understood that the present invention embraces all enantiomers and their mixtures. Enantiomers are preferred over racemates. Similar considerations apply in relation to starting materials exhibiting asymmetric carbon atoms as mentioned.

Alkyl or alkoxy may be straight or branched.

Halogen may be F, Cl, Br or I, preferably F, Cl or Br.

By heterocyclic residue is meant a three to eight, preferably five to eight, membered saturated, unsaturated or aromatic heterocyclic ring comprising 1 or 2 heteroatoms, preferably selected from N, O and S, and optionally substituted. Suitable examples include e.g. pyridyl, e.g. 3 or 4-pyridyl, piperidyl, e.g. piperidin-1-yl, 3- or 4-piperidyl, homopiperidyl, piperazinyl, homopiperazinyl, morpholin-4-yl, imidazolyl, imidazolidinyl, pyrrolyl or pyrrolidinyl, optionally substituted, e.g. mono- or polysubstituted. When the heterocyclic residue is substituted, this may be on one or more ring carbon atoms and/or on a ring nitrogen atom when present. Examples of a substituent on a ring carbon atom include e.g. C$_{1-4}$alkyl e.g. CH$_3$;

C$_{3-6}$cycloalkyl e.g. cyclopropyl, optionally further substituted by C$_{1-4}$alkyl;

wherein p is 1, 2 or 3, preferably 1; CF$_3$; halogen; OH; NH$_2$; —CH$_2$—NR$_7$R$_8$ wherein each of R$_7$ and R$_8$, independently, is H, C$_{1-4}$alkyl, or R$_7$ and R$_8$ form together with the nitrogen atom to which they are bound a heterocyclic residue or a heteroaryl; —CH$_2$—OH; piperidin-1-yl; or pyrrolidinyl. Examples of a substituent on a ring nitrogen atom are e.g. C$_{1-6}$alkyl; acyl, e.g. R'$_x$—CO wherein R'$_x$ is H, C$_{1-6}$alkyl or phenyl optionally substituted by C$_{1-4}$alkyl, C$_{1-4}$alkoxy or amino, e.g formyl; C$_{3-6}$cycloalkyl; C$_{3-6}$cycloalkyl-C$_{1-4}$alkyl; phenyl; phenyl-C$_{1-4}$alkyl e.g. benzyl; a heterocyclic residue, e.g. as disclosed above, e.g. an aromatic heterocyclic residue comprising 1 or 2 nitrogen atoms; or a residue of formula β

 —R$_5$-Z   (β)

wherein R$_5$ is C$_{1-4}$alkylene or C$_{2-4}$alkylene interrupted by O and Z is OH, NH$_2$, NH(C$_{1-4}$alkyl) or N(C$_{1-4}$alkyl)$_2$.

When the substituent on a cyclic nitrogen is a heterocyclic residue, it may be a five or six membered saturated, unsaturated or aromatic heterocyclic ring comprising 1 or 2 heteroatoms, preferably selected from N, O and S. Examples include e.g. 3- or 4-pyridyl, piperidyl, e.g. piperidin-1-yl, 3- or 4-piperidyl, homopiperidyl, piperazinyl, homopiperazinyl, pyrimidinyl, morpholin-4-yl, imidazolyl, imidazolidinyl, pyrrolyl or pyrrolidinyl.

Further examples of heterocyclic residue as R$_{10}$, R$_{10a}$ or Y include e.g. a residue of formula (γ)

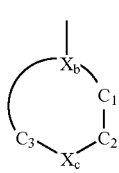

(γ)

wherein
the ring D is a 5, 6 or 7 membered saturated, unsaturated or aromatic ring;
$X_b$ is —N=, —C= or —CH—;
$X_c$ is —N=, —NR$_f$—, —CR$_f'$= or —CHR$_f'$— wherein R$_f$ is a substituent as indicated above for a ring nitrogen atom, and R$_f'$ is a substituent as indicated above for a ring carbon atom;
the bond between $C_1$ and $C_2$ is either saturated or unsaturated;
each of $C_1$ and $C_2$, independently, is a carbon atom which is optionally substituted by one or two substituents selected among those indicated above for a ring carbon atom; and
the line between $C_3$ and $X_b$ and between $C_1$ and $X_b$, respectively, represents the number of carbon atoms as required to obtain a 5, 6 or 7 membered ring D,
whereby when Y is a residue of formula (γ) at least one of $X_b$ and $X_c$ is —N=.

A preferred residue of formula (γ) is one wherein the ring D forms a 1,4-piperazinyl ring optionally C— and/or N-substituted as indicated.

Representative examples of a residue of formula (γ) are e.g. 3- or 4-pyridyl; piperidin-1-yl; 1-N—($C_{1-4}$alkyl)- or -(ω-hydroxy-$C_{1-4}$alkyl)-3-piperidyl; morpholin-4-yl; imidazolyl; pyrrolidinyl; 1-piperazinyl; 2-$C_{1-4}$alkyl- or —$C_{3-6}$cycloalkyl-1-piperazinyl; 3-$C_{1-4}$alkyl- or —$C_{3-6}$cycloalkyl-1-piperazinyl; 2,2- or 3,5- or 2,5- or 2,6-di($C_{1-4}$alkyl)-1-piperazinyl; 3,4,5-tri-($C_{1-4}$alkyl)-1-piperazinyl; 4-N—($C_{1-4}$alkyl)- or -(ω-hydroxy-$C_{1-4}$alkyl)- or (ω-dimethylamino-$C_{1-4}$ alkyl)-1-piperazinyl; 4-N-pyridin-4-yl-1-piperazinyl; 4-N-phenyl- or —$C_{3-6}$cycloalkyl-1-piperazinyl; 4-N—($C_{1-4}$alkyl)- or -(ω-hydroxy-$C_{1-4}$alkyl)-3-$C_{1-4}$alkyl- or -3,3-di($C_{1-4}$ alkyl)-1-piperazinyl; 4-N-(1-$C_{1-4}$alkyl-$C_{3-6}$cycloalkyl)-1-piperazinyl; 4-N-formyl-1-piperazinyl; 4-N-pyrimidin-2-yl-1-piperazinyl; or 4-N—$C_{1-4}$alkyl-1-homopiperazinyl.

In the compounds of formula I, the following significances are preferred individually or in any sub-combination:
1. $R_a$ is H or methyl;
2. one of $R_b$, $R_c$, $R_d$ and $R_e$ is methyl or ethyl and the other three substituents are H; or $R_b$, $R_c$, $R_d$ and $R_e$ are all H;
3. each of $R_2$, $R_{20}$ and $R_{20a}$, independently, is H, Cl, $NO_2$, F, $CF_3$ or methyl;
4. n is o or 1;
5. each of $R_3$ and $R_4$, independently, is H, methyl, ethyl or i-propyl; or $R_3$ and $R_4$ form together with the nitrogen atom to which they are bound a heterocyclic residue e.g. an optionally substituted piperazinyl or pyrrolidinyl; and
6. each of $R_{10}$, $R_{10}$ and $R_{10a}$ is a heterocyclic residue, preferably a piperazin-1-yl optionally substituted by $CH_3$ in position 3 and/or 4 or in position 3 by ethyl; —$CH_2NR_7R_8$, $C_{1-4}$alkoxy-$C_{1-4}$alkyl or halogeno-$C_{1-4}$alkyl; even more preferably piperazin-1-yl substituted by $CH_3$ in position 4.

The present invention also includes a process for the preparation of a compound of formula I which process comprises reacting a compound of formula II

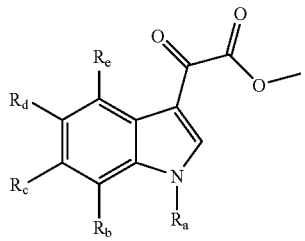

II wherein $R_a$ to $R_e$ are as defined above,
with a compound of formula III

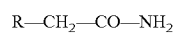

R—$CH_2$—CO—$NH_2$ (III)

wherein R is as defined above, and, where required, converting the resulting compound of formula I obtained in free form to a salt form or vice versa, as appropriate.

The process may conveniently be effected in the presence of a strong base, e.g. t-BuOK, e.g. as disclosed in WO02/38561 or WO 03/08259, the contents of which being incorporated herein by reference, and as illustrated in the Examples.

Compounds of formula II and III may be prepared in accordance with known methods, e.g. as disclosed in WO02/38561 or WO 03/08259, the contents of which being incorporated herein by reference, and as illustrated in the Examples.

Further examples of selective PKC inhibitors according to the present invention are e.g. compounds of formula Ib.

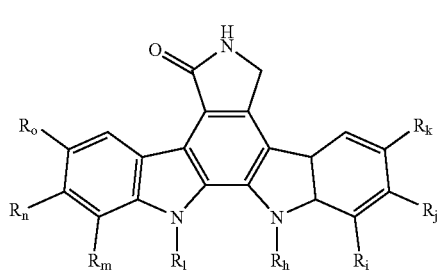

Ib wherein each of $R_i$, $R_j$, $R_k$, $R_l$, $R_m$, $R_n$ and $R_o$, independently, is H or an $C_{1-10alkyl}$; $R_h$ is $(CH_2)_n$—CN, and n' is 0 to 5.

In the compounds of formula Ib, the following significances are preferred individually or in any sub-combination:
1—$R_i$, $R_j$, $R_k$, $R_m$, $R_n$ and $R_o$ are all H;
2—$R_l$ is $CH_3$; and
3—$R_h$ is $(CH_2)_2$—CN.

The compound of formula Ib wherein $R_i$, $R_j$, $R_k$, $R_m$, $R_n$ and $R_o$ are all H, $R_l$ is $CH_3$ and $R_h$ is $(CH_2)_2$—CN is well known in the art, and disclosed e.g. in Martin-Baron et al., The Journal of Biological Chemistry (1993), 268 (13), pp 9194-9197, the content thereof being incorporated by reference.

The compounds of formula Ib, in particular the compound of formula Ib wherein $R_i$, $R_j$, $R_k$, $R_m$, $R_n$ and $R_o$ are all H, $R_l$ is $CH_3$ and $R_h$ is $(CH_2)_2$—CN, may be selective PKC inhibitors, e.g. selective inhibitors for the isoforms α and β of the PKC over the other existing PKC isoforms.

The compounds of the invention, e.g. compounds of formula I or Ib, may exist in free form or in salt form, e.g. salts with e.g. organic or inorganic acids, for example, hydrochloric acid, acetic acid, trifluoroacetic acid.

Insofar as the production of the starting materials is not particularly described, the compounds are known or may be prepared analogously to methods known in the art or as described hereafter.

The following examples are illustrative of the invention without any limitation.

AcOH=acetic acid
DDQ=2,3-dichloro-5,6-dicyano-1,4-benzoquinone
DMF=dimethylformamide
EtOAc=ethylacetate
MeOH=methanol
Pd$_2$(dba)$_3$=Pd(0)-bis(dibenzylidenacetone)
TBAF=tetrabutyl ammonium fluoride
THF=tetrahydrofuran
FCC=flash column chromatography
TLC=thin layer chromatography.
RT=room temperature

EXAMPLE 1

3-(2-Chloro-7-dimethylaminomethyl-naphthalen-1-yl)-4-(1-methyl-1H-indol-3-yl)-pyrrole-2,5-dione

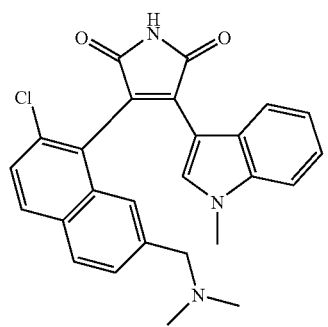

Activated 3 Å molecular sieve (2.0 g) is added to a solution of 2-(2-Chloro-7-dimethylaminomethyl-naphthalen-1-yl)-acetamide (1.0 g, 3.61 mmol) and (1-Methyl-1H-indol-3-yl)-oxo-acetic acid methyl ester (1.02 g, 4.69 mmol) in dry THF (50 ml) under an atmosphere of argon. A solution of 1.0 M KOtBu in THF (10.9 ml, 10.9 mmol) is then added in one portion at RT. After 1 h at RT, TLC analysis indicates complete conversion of starting materials. The reaction mixture is diluted with EtOAc and poured into a saturated aqueous NH$_4$Cl solution. The organic layer is separated, washed with brine, dried over Na$_2$SO$_4$, and the organic solvent is evaporated. The residue is purified by FCC (EtOAc/AcOH/H$_2$O 600:150:150) to afford the title compound, which is dissolved in glacial AcOH and lyophilized. The title compound is obtained as the water soluble bis-acetate salt. $^1$H NMR (d$_6$-DMSO, 400 MHz): δ 1.80 (s, 6H), 3.20-3.42 (m, 2H), 6.10 (d, J=9.0 Hz, 1H), 6.44 (t, J=9.0 Hz, 1H), 6.94 (t, J=9.0 Hz, 1H), 7.31 (d, J=9.0 Hz, 1H), 7.34 (d, J=9.0 Hz, 1H), 7.42 (s, 1H), 7.63 (d, J=10.8 Hz, 1H), 7.89 (d, J=9.6 Hz, 1H), 8.03 (d, J=9.0 Hz, 1H), 8.10 (s, 1H), 11.0-11.3 (br, 1H). ES$^+$–MS: 444, 446 [M+H]$^+$.

Preparation of 2-(2-Chloro-7-dimethylaminomethyl-naphthalen-1-yl)-acetamide (2-Chloro-7-dimethylaminomethyl-naphthalen-1-yl)-acetic acid ethyl ester (2.70 g, 8.82 mmol) and formamide (1.17 ml, 29.57 mmol) are dissolved under an atmosphere of argon in dry DMF (25 ml). The solution is heated to 105° C., and NaOMe (1.64 ml of a 5.4 M solution in MeOH, 8.82 mmol) is added dropwise during 10 minutes. After 1 hour at 105° C., TLC analysis indicates complete consumption of starting material. The reaction mixture is cooled to RT, diluted with water, and adjusted to a pH of 6-7 by the addition of 1 M NaHSO$_4$ solution. The mixture is concentrated and purified by FCC (CH$_2$Cl$_2$/EtOH/NH$_3$ conc. 90:9:1) to yield the title compound. $^1$H NMR (d$_6$-DMSO, 400 MHz): δ 2.01 (s, 6H), 3.48 (s, 3H), 4.02 (s, 3H), 6.9-7.0 (br, 1H), 7.41-7.47 (m, 2H); 7.47-7.85 (br, 1H), 7.75-7.88 (m, 2H), 7.80 (d, J=12.1 Hz, 1H). ES$^+$–MS: 277.3, 279.2 [M+H]$^+$.

Preparation of (2-Chloro-7-dimethylaminomethyl-naphthalen-1-yl)-acetic acid ethyl ester Dimethylamine (5.6 M solution in EtOH, 4.2 ml, 23.20 mmol) is added under an atmosphere of argon to a solution of (2-Chloro-7-formyl-naphthalen-1-yl)-acetic acid ethyl ester (4.28 g, 15.46 mmol) in THF (80 ml). The mixture is stirred at RT for 18 h, before a solution of sodium cyanoborohydride (1.16 g, 18.56 mmol) in MeOH (20 ml) and glacial acetic acid (4.4 ml, 77.33 mmol) are added. After stirring at RT for 2 h, TLC analysis indicates complete consumption of starting material. The reaction mixture is diluted with water and adjusted to pH 8-9 by the addition of conc. aq. NaHCO$_3$ solution. Extraction with EtOAc, washing with brine, drying over Na$_2$SO$_4$ and removal of solvent yields the crude reaction product. Purification by FCC (EtOAc, then EtOAc/MeOH 4:1) affords the title compound. $^1$H NMR (CDCl$_3$, 400 MHz): δ 1.26 (t, J=8.8 Hz, 3H), 2.28 (s, 6H), 3.62 (s, 3H), 4.18 (q, J=8.8 Hz, 2H), 4.32 (s, 3H), 7.48 (d, J=9.9 Hz, 1H), 7.52 (d, J=9.9 Hz, 1H), 7.73 (d, J=9.9 Hz, 1H), 7.80-7.84 (m, 2H). ES$^+$–MS: 306.3, 308.2. [M+H]$^+$.

Preparation of (2-Chloro-7-formyl-naphthalen-1-yl)-acetic acid ethyl ester (2-Chloro-7-cyano-naphthalen-1-yl)-acetic acid ethyl ester (5.53 g, 20.20 mmol) is dissolved in a mixture of water (70 ml), pyridine (130 ml) and glacial acetic acid (70 ml). Sodium hypophosphite (17.13 g, 161.62 mmol) and Raney nickel (13 g) are added at RT. The reaction mixture is heated to 100° C. for 1 h. TLC analysis indicates complete consumption of starting material. The reaction mixture is cooled to RT, filtered through Celite and concentrated on a rotary evaporator. The residue is taken up in 2 M aqueous HCl. Extraction with EtOAc, removal of solvent and purification by FCC (hexane/EtOAc 5:1) yields the title compound. $^1$H NMR (CDCl$_3$, 400 MHz): δ 1.28 (t, J=8.8 Hz, 3H), 4.22 (q, J=8.8 Hz, 2H), 4.39 (s, 2H), 7.68 (d, J=9.9 Hz, 1H), 7.83 (d, J=9.9 Hz, 1H), 7.95-8.03 (m, 2H), 8.48 (s, 1H), 10.2 (s, 1H). ES$^-$–MS: 275.3, 277.3 [M+H]$^+$.

Preparation of (2-Chloro-7-cyano-naphthalen-1-yl)-acetic acid ethyl ester (2-Chloro-7-trifluoromethanesulfonyloxy-naphthalen-1-yl)-acetic acid ethyl ester (9.30 g, 23.43 mmol) is dissolved in DMF (80 ml) under an atmosphere of argon. Palladium(0) tetrakis(triphenylphosphane) (1.08 g, 0.9375 mmol) and zinc (II) cyanide (5.50 g, 46.87 mmol) are added. The reaction mixture is heated to 125° C. After 1 h, TLC analysis indicates complete consumption of starting material. The suspension is cooled to RT and poured onto water. After stirring for 15 minutes, filtration and concentration affords the crude reaction product. Purification by FCC (hexane/EtOAc 4:1) affords the title compound. $^1$H NMR (CDCl$_3$, 400 MHz): δ 1.26 (t, J=8.8 Hz, 3H), 4.19 (q, J=8.8 Hz, 2H), 4.28 (s, 2H), 7.62-7.66 (m, 2H), 7.79 (d, J=9.9 Hz, 1H), 7.92 (d, J=9.9 Hz, 1H), 8.32 (s, 1H). ES$^+$-MS; 274.2 [M+H]$^+$.

Preparation of (2-Chloro-7-trifluoromethanesulfonyloxy-naphthalen-1-yl)-acetic acid ethyl ester (2-Chloro-7-hydroxy-naphthalen-1-yl)-acetic acid ethyl ester (8.03 g, 30.33 mmol) is dissolved under an atmosphere of argon in pyridine (60 ml). After cooling to 0° C., trifluoromethanesulfonic acid anhydride (5.50 ml, 33.36 mmol) is added dropwise during 15 minutes. After stirring at 0° C. for 15 minutes and at RT for 1 h, TLC analysis indicates complete consumption of starting material. The reaction mixture is poured into 1 M aqueous NaHCO$_3$ solution. After extraction with EtOAc, washing with brine and drying of the organic layer over Na$_2$SO$_4$, concentration yields the crude reaction product. Purification by FCC (hexane/EtOAc 4:1) affords the title compound. $^1$H NMR (CDCl$_3$, 400 MHz): δ 1.13 (t, J=9.4 Hz, 3H), 4.08 (q, J=9.4 Hz, 2H), 4.15 (s, 2H), 7.28-7.30 (m, 1H), 7.48 (d, J=11 Hz, 1H), 7.69 (d, J=11 Hz, 1H), 7.72 (m, 1H), 7.82 (d, J=11 Hz, 1H). ES$^+$-MS: 414.2, 41.6.0, 397.1 [M+H]$^+$.

Preparation of (2-Chloro-7-hydroxy-naphthalen-1-yl)-acetic acid ethyl ester (2-Chloro-7-methoxy-naphthalen-1-yl)-acetic acid ethyl ester (12.0 g, 43.10 mmol) and tetrabutylammonium iodide (20.7 g, 56.04 mmol) are dissolved under an atmosphere of argon in CH$_2$Cl$_2$ (240 ml). The reaction mixture is cooled to −78° C. and a 1 M solution of BBr$_3$ in CH$_2$Cl$_2$ (108 ml, 107.77 mmol) is added during 30 minutes. After stirring at −78° C. for 15 minutes and at RT for 1 h, TLC analysis indicates complete consumption of starting material. A sat. aqueous solution of NaHCO$_3$ (8 ml) is carefully added. The organic layer is separated, washed with brine, dried over Na$_2$SO$_4$ and concentrated. Purification by FCC (hexane/EtOAc 4:1 to 3:2) yields the title compound. $^1$H NMR (CDCl$_3$, 400 MHz): δ 1.51 (t, J=9.9 Hz, 3H), 4.43 (q, J=9.9 Hz, 2H), 4.48 (s, 2H), 6.28-6.36 (br, 1H), 7.29-7.32 (m, 1H), 7.48-7.49 (m, 1H), 7.58 (d, J=10 Hz, 1H), 7.89 (d, J=10 Hz, 1H), 7.96 (d, J=10 Hz, 1H). ES$^+$-MS: 265.2, 267.2 [M+H]$^+$.

Preparation of (2-Chloro-7-methoxy-naphthalen-1-yl)-acetic acid ethyl ester

A mixture of [2-Chloro-7-methoxy-3,4-dihydro-2H-naphthalen-(1E/Z)-ylidene]-acetic acid ethyl ester and of (2-Chloro-7-methoxy-3,4-dihydro-naphthalen-1-yl)-acetic acid ethyl ester (26.82 g, 95.52 mmol) is dissolved under an atmosphere of argon in dioxane (280 ml). 2,3-Dichloro-5,6-dicyano-p-benzoquinone (DDQ, 47.70 g, 210.16 mmol) is added, and the reaction mixture is refluxed for 2 h. TLC analysis indicates complete conversion of starting material. After cooling to RT, addition of MeOH renders the reaction mixture homogeneous. Silica gel (250 g) is added, and the solvent is removed by rotary evaporation. Purification by FCC (hexane/EtOAc 9:1) yields the title compound. $^1$H NMR (CDCl$_3$, 400 MHz): δ 1.24 (t, J=8.8 Hz, 3H), 3.95 (s, 3H), 4.19 (q, J=8.8 Hz, 2H), 4.28 (s, 2H), 7.16-7.19 (m, 1H), 7.22 (s, 1H), 7.38 (d, J=10 Hz, 1H), 7.68 (d, J=10 Hz, 1H), 7.75 (d, J=10 Hz, 1H). ES$^+$-MS: 279.2, 281.2 [M+H]$^+$.

Preparation of (2-Chloro-7-methoxy-3,4-dihydronaphthalen-1-yl)-acetic acid ethyl ester (2-Chloro-1-hydroxy-7-methoxy-1,2,3,4-tetrahydronaphthalen-1-yl)-acetic acid ethyl ester (42.7 g, 142.9 mmol) is dissolved under an atmosphere of argon in pyridine (250 ml). Trifluoromethanesulfonic acid anhydride (30.7 ml, 185.8 mmol) is added during 30 minutes, while keeping the temperature at 25° C. with occasional cooling with a ice bath. After addition is complete, the reaction mixture is warmed to 50° C. for 2 h. TLC analysis indicates complete conversion of starting material. 2 M aqueous HCl (100 ml) is carefully added, and then the reaction mixture is concentrated to dryness on the rotary evaporator. The residue is taken up in 2 M aqueous HCl (100 ml) and extracted with EtOAc. The organic layer is dried over Na$_2$SO$_4$ and concentrated. Purification by FCC (EtOAc) affords the title compound. ES$^+$-MS: 281.2, 283.2 [M+H]$^+$.

Preparation of (2-Chloro-1-hydroxy-7-methoxy-1,2,3,4tetrahydro-naphthalen-1-yl)-acetic acid ethyl ester A solution of EtOAc (16.1 ml, 164.48 mmol) in THF (250 ml) is slowly added under an atmosphere of argon at −78° C. to a solution of lithium diisopropylamine (prepared from 23.3 ml of diisopropylamine (164.48 mmol) and 102.8 ml of 1.6 M n-BuLi in hexane (164.48 mmol) in THF (250 ml). After stirring at −78° C. for 30 minutes, a solution of 2-chloro-7-methoxy-3,4-dihydro-2H-naphthalen-1-one (31.5 g, 149.53 mmol) in THF (250 ml) is slowly added during 30 minutes. The reaction mixture is stirred at −78° C. for 1 h. TLC analysis indicates complete conversion of starting material. A sat. aqueous solution of NH$_4$Cl (250 ml) is carefully added to the reaction mixture at −78° C. The mixture is warmed to RT. The organic layer is separated, diluted with EtOAc and washed with brine. After drying over Na$_2$SO$_4$, the solvent is removed. Purification by FCC (hexane/EtOAc 4:1) yields the title compound. $^1$H NMR (CDCl$_3$, 400 MHz): δ 1.27 (t, J=9.4 Hz, 3H), 2.32-2.48 (m, 2H), 2.78-2.88 (m, 1H), 2.86-3.02 (m, 2H), 3.05-3.14 (m, 1H), 3.82 (s, 3H), 4.18 (q, J=9.4 Hz, 2H), 5.02-5.08 (m, 1H), 6.81-6.84 (m, 1H), 7.03 (d, J=10.5 Hz, 1H), 7.18-7.19 (m, 1H). ES$^+$-MS: 281.3, 283.3 [M+H—H$_2$O]$^+$.

Preparation of 2-Chloro-7-methoxy-3,4-dihydro-2H-naphthalen-1-one

A solution of 7-Methoxy-3,4-dihydro-2H-naphthalen-1-one (25.6 g, 145.28 mmol) in THF (300 ml) is slowly added under an atmosphere of argon at −78° C. to a solution of lithium diisopropyl amine in THF (300 ml; prepared from 22.6 ml of diisopropylamine (160 mmol) and 100 ml of 1.6 M n-BuLi in hexane (160 mmol)). After 30 minutes at −78° C., a solution of para-tolylsulfonyl chloride (30.5 g, 159.8 mmol) in THF (300 ml) is added during 20 minutes. The dry ice cooling bath is removed, and the reaction mixture is allowed to reach RT. After 1 h, TLC analysis indicates complete consumption of starting material. A sat. aqueous solution of NH$_4$Cl (100 ml) is added, and the mixture is stirred at RT for 15 minutes. The organic layer is separated, washed with brine, dried over Na$_2$SO$_4$ and concentrated. Purification by FCC (hexane/EtOAc 3:1) yields the title compound. $^1$H NMR (CDCl$_3$, 400 MHz): δ 2.32-2.52 (m, 2H), 2.82-2.90 (m, 2H), 3.10-3.18 (m, 2H), 3.78 (s, 1H), 4.52-4.58 (m, 1H), 7.01-7.05 (m, 1H), 7.11 (d, J=8.8 Hz, 1H), 7.47-7.48 (m, 1H). ES$^+$–MS: 211.3, 213.3 [M+H]$^+$.

By following the procedure of Example 1, but using the appropriate starting materials, the compounds of formula A wherein R$_a$, R$_b$, R$_c$, R$_d$, R$_3$ and R$_4$ are as indicated in Table 2 below, and R$_e$ is H, may be obtained.

TABLE 1

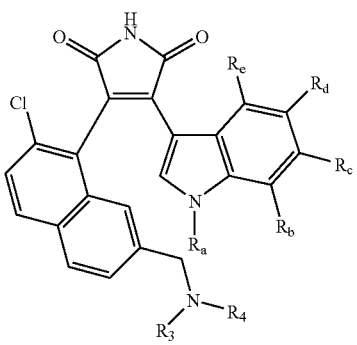

A

| | R$_3$ | R$_4$ | R$_a$ | R$_b$ | R$_c$ | R$_d$ | MS |
|---|---|---|---|---|---|---|---|
| 2. | H | H | CH$_3$ | H | H | H | MH$^+$ 417 |
| 3. | H | CH$_3$ | H | H | H | H | MH$^+$ 417 |
| 4. | H | CH$_3$ | CH$_3$ | H | H | H | MH$^+$ 431 |
| 5. | H | CH$_3$ | H | CH$_3$ | H | H | MH$^+$ 431 |
| 6. | H | CH$_3$ | H | H | CH$_3$ | H | MH$^+$ 431 |
| 7. | H | CH$_3$ | H | H | H | CH$_3$ | MH$^+$ 445 |
| 8. | CH$_3$ | CH$_3$ | H | CH$_3$ | H | H | MH$^+$ 444 |
| 9. | CH$_3$ | CH$_3$ | H | H | H | H | MH$^+$ 431 |
| 10. | CH$_3$ | CH$_3$ | H | H | CH$_3$ | H | MH$^+$ 445 |
| 11. | CH$_3$ | CH$_3$ | H | H | H | CH$_3$ | MH$^+$ 445 |
| 12. | CH$_3$ | CH$_2$CH$_3$ | CH$_3$ | H | H | H | MH$^+$ 459 |
| 13. | CH$_2$CH$_3$ | CH$_2$CH$_3$ | CH$_3$ | H | H | H | MH$^+$ 473 |
| 14. | H | CH$_2$CH$_3$ | CH$_3$ | H | H | H | MH$^+$ 445 |
| 15. | H | i-propyl | CH$_3$ | H | H | H | MH$^+$ 459 |
| 16. | —CH$_2$—CH$_2$—N(CH$_3$)—CH$_2$—CH$_2$— | | CH$_3$ | H | H | H | MH$^+$ 500 |
| 17. | —CH$_2$—CH$_2$—CH$_2$—CH$_2$— | | CH$_3$ | H | H | H | MH$^+$ 471 |

By following the procedure of Example 1, but using the appropriate starting materials, the compounds of formula B wherein R$_c$, R$_d$ and R$_e$ are H; and R$_a$, R$_b$, R$_3$ and R$_4$ are as indicated in Table 2 below, may be obtained.

TABLE 2

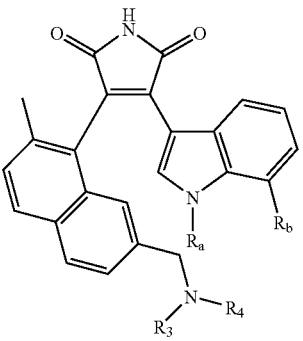

B

| | R$_3$ | R$_4$ | R$_a$ | R$_b$ | MS |
|---|---|---|---|---|---|
| 18. | H | H | CH$_3$ | CH$_3$ | MH$^+$ 410 |
| 19. | H | H | H | CH$_3$ | MH$^+$ 396 |
| 20. | H | H | H | H | MH$^+$ 382 |
| 21. | H | H | CH$_3$ | H | MH$^+$ 396 |

By following the procedure of Example 1, but using the appropriate starting materials, the compounds of formula B wherein R$_b$, R$_e$, R$_d$ and R$_e$ are H; and R$_a$, R$_3$ and R$_4$ are as indicated in Table 3 below, may be obtained.

TABLE 3

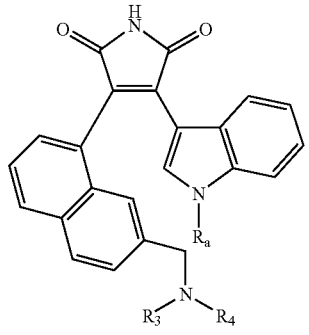

B

| | R$_3$ | R$_4$ | R$_a$ | MS |
|---|---|---|---|---|
| 22. | H | H | H | MH$^+$ 368 |
| 23. | H | H | CH$_3$ | MH$^+$ 382 |

By following the procedure of Example 1, but using the appropriate starting materials, the compounds of formula C wherein R$_b$, R$_c$, R$_d$ and R$_e$ are H; and R$_e$, R$_3$ and R$_4$ are as indicated in Table 4 below, may be obtained.

TABLE 4

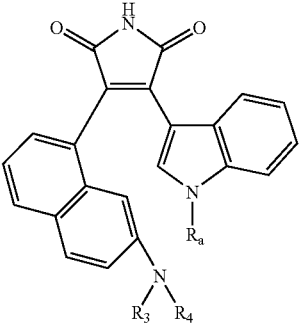

| | $R_3$ | $R_4$ | $R_a$ | MS |
|---|---|---|---|---|
| 24. | H | H | $CH_3$ | $MH^+$ 368 |
| 25. | H | H | H | $MH^+$ 354 |

By following the procedure of Example 1, but using the appropriate starting materials, the compounds of formula D wherein $R_b$ is as indicated in Table 5 below, may be obtained.

TABLE 5

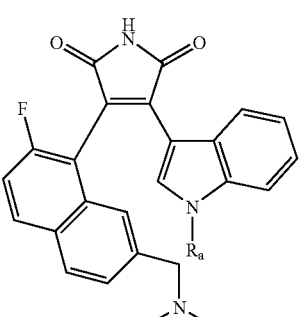

| | $R_b$ | MS |
|---|---|---|
| 26. | $CH_3$ | $MH^+$ 428 |
| 27. | H | $MH^+$ 414 |

EXAMPLE 28

3-(7-Methyl-1H-indol-3-yl)-4-[5-(4-methyl-piperazin-1-yl)-pyridin-3-yl]-pyrrole-2,5-dione

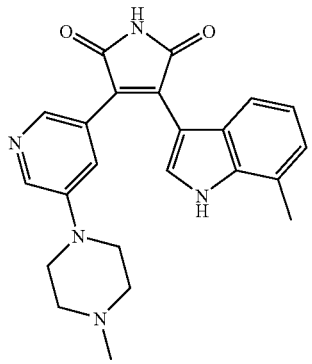

2-[5-(4-Methyl-piperazin-1-yl)-pyridin-3-yl]-acetamide (150 mg, 0.64 mmol) and (7-methyl-1H-indol-3-yl)-oxo-acetic acid methyl ester (209 mg, 0.96 mmol) are dissolved under an atmosphere of argon in a mixture of dry DMF (2 ml) and dry THF (2 ml). A solution of 1.0 M KOtBu in THF (1.9 ml, 1.9 mmol) is then added at RT. After 1 h at 50° C., TLC analysis indicated complete conversion of starting materials. The reaction mixture is diluted with EtOAc and poured into a saturated aqueous $NH_4Cl$ solution. The organic layer is separated, washed with brine, dried over $Na_2SO_4$, and the organic solvent is evaporated. The residue is purified by FCC (EtOAc/AcOH/$H_2O$ 600:115:150) to afford the title compound. $^1H$ NMR ($d_6$-DMSO 400 MHz): δ 2.15 (s, 3H), 2.28-2.32 (m, 2H), 2.92-3.00 (m, 2H), 3.15 (s, 3H), 6.21 (d, J=9 Hz, 1H), 6.64 (t, J=9 Hz, 1H), 6.88 (d, J=9 Hz, 1H), 7.22 (s, 1H), 7.98 (br s, 1H), 8.20-8.22 (m, 1H). $ES^+$-MS: 402.6 $[M+H]^+$.

Preparation of 2-[5-(4-Methyl-piperazin-1-yl)-pyridin-3-yl]-acetamide

[5-(4-Methyl-piperazin-1-yl)-pyridin-3-yl]-acetic acid (1.57 g, 5.78 mmol) and carbonyl diimidazole (1.03 g, 6.36 mmol) are dissolved under an atmosphere of argon in DMF (16 ml). After stirring at RT for 1 h, aqueous $NH_4OH$ (25%, 16 ml) is added, and stirring at RT is continued for 15 minutes. TLC analysis indicated complete consumption of starting material. The aqueous layer is saturated with NaCl and extracted repeatedly with $CH_2Cl_2$. The organic layers are dried over $Na_2SO_4$ and concentrated. Purification by FCC ($CH_2Cl_2$:MeOH 95:5 to 90:10 to 80:20 to 70:30 to 50:50 to 25:75 to 0:100) yields the title compound. $^1H$ NMR ($d_6$-DMSO 400 MHz): δ 2.76 (s, 3H), 3.12-3.42 (m, 8H), 3.34 (s, 2H), 6.86-6.96 (br s, 1H), 7.26 (s, 1H), 7.93 (s, 1H), 8.21 (s, 1H). $ES^+$-MS: 235.4 $[M+H]^+$.

Preparation of [5-(4-Methyl-piperazin-1-yl)-pyridin-3-yl]-acetic acid

[5-(4-Methyl-piperazin-1-yl)-pyridin-3-yl]-acetic acid tert-butyl ester (1.68 g, 5.77 mmol) is dissolved in 4 M HCl in dioxane (28 ml). After 1 h at 60° C., TLC analysis indicated complete consumption of starting material. The reaction mixture is cooled to RT and diluted with $Et_2O$. The precipitate is filtered and washed with $Et_2O$ to yield the title compound, which is used in the next reaction without further purification. $^1H$ NMR ($d_6$-DMSO 400 MHz): δ 2.79 (s, 3H), 3.05-4.10 (br m, 8H), 3.81 (s, 2H), 8.04 (s, 1H), 8.22 (s, 1H), 8.45 (s, 1H). $ES^+$-MS: 236.4 $[M+H]^+$.

Preparation of 2-[5-(4-Methyl-piperazin-1-yl)-pyridin-3-yl]-acetamide[5-(4-Methyl-piperazin-1-yl)-pyridin-3-yl]-acetic acid tert-butyl ester Potassium phosphate (4.08 g, 19.21 mmol) is dried under high vacuum at 100° C. for 90 minutes. After cooling to RT and venting with argon, $Pd_2(dba)_3$ (70 mg, 0.077 mmol), dicyclohexyl-(2',4',6'-triisopropyl-biphenyl-2-yl)-phosphane (183 mg, 0.38 mmol), a degassed mixture of toluene/tert-butanol (9:1, 20 ml) and N-methyl piperazine (1.15 g, 11.53 mmol) are added. The reaction mixture is immersed in a pre-heated oil bath (100° C.). After 2 h at 100° C., additional $Pd_2(dba)_3$ (70 mg, 0.077 mmol) and dicyclohexyl-(2',4',6'-triisopropyl-biphenyl-2-yl)-phosphane (183 mg, 0.38 mmol) are added. After an additional 2 h at 100° C., TLC analysis indicated complete conversion of starting material. The reaction mixture is cooled to RT, diluted with water and extracted with $CH_2Cl_2$. The combined organic layers are dried over $Na_2SO_4$ and concentrated. Purification by FCC ($CH_2Cl_2$:MeOH 95:5 to 92:8 to 88:12 to 80:20) yields the title compound. $^1$H NMR (CDCl$_3$, 400 MHz): δ 1.57 (s, 9H), 2.48 (s, 3H), 2.68-2.72 (m, 4H), 3.35-3.40 (m, 4H), 3.60 (s, 2H), 7.24-7.27 (m, 1H), 8.10 (br s, 1H), 8.32-8.33 (m, 1H). ES$^+$–MS: 292.4 [M+H]$^+$.

Preparation of (5-Chloro-pyridin-3-yl)-acetic acid tert-butyl ester

Pd$_2$(dba)$_3$ (928 mg, 1.01 mmol) and (2'-dicyclohexylphosphanyl-biphenyl-2-yl)-dimethyl-amine (838 mg, 2.13 mmol) are added at RT under an atmosphere of argon to a solution of lithium hexamethyl disilazide in toluene (prepared by addition of n-BuLi (1.6 M in hexane, 24.3 ml, 38.85 mmol) to hexamethyl disilazane (6.27 g, 38.85 mmol) in toluene (100 ml) at −78° C.). The mixture is stirred at RT for 10 minutes, then it is cooled to −10° C. Acetic acid tert-butyl ester (4.12 g, 35.48 mmol) is added during 10 minutes. This mixture is canulated into a cold (−10° C.) solution of 1,3-dichloropyridine (5.00 g, 33.79 mmol) in toluene (40 ml). The mixture is warmed to RT and stirred for 2 h. TLC analysis indicated substantial conversion of starting material. Water was added, the resulting slurry is filtered, and the filtrate is extracted with EtOAc. The combined organic layers are dried over Na$_2$SO$_4$ and concentrated. Purification by FCC (hexane/EtOAc 100:0 to 92:8 to 85:15) yields the title compound. $^1$H NMR (CDCl$_3$, 400 MHz): δ 1.39 (s, 9H), 3.47 (s, 2H), 7.58-7.60 (m, 1H), 8.31 (s,1H), 8.41-8.42 (m, 1H). ES$^+$–MS: 228.3 [M+H]$^+$.

EXAMPLE 29

3-(7-Methyl-1H-indol-3-yl)-4-[2-methyl-5-(4-methyl-piperazin-1-yl)-pyridin-3-yl]-pyrrole-2,5-dione

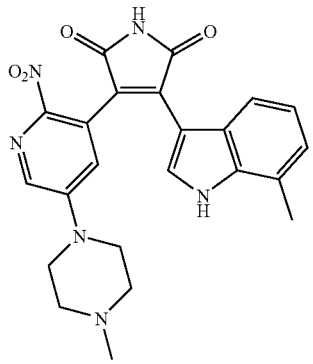

To a solution of 2-[5-(4-Methyl-piperazin-1-yl)-2-nitro-pyridin-3-yl]-acetamide (96 mg, 0.34 mmol) and (7-Methyl-1H-indol-3-yl)-oxo-acetic acid methyl ester (127 mg, 0.58 mmol) in dry THF (8.0 mL) is added at 0° C. under an atmosphere of argon, a solution of 1.0 M KOtBu in THF (1.7 ml, 1.7 mmol). After stirring for 2 h at 0° C., TLC analysis indicated complete consumption of the starting materials. The reaction mixture is diluted with EtOAc and washed with brine. The aqueous phase is extracted with EtOAc and the combined organic layers are washed with brine, dried over Na$_2$SO$_4$, and concentrated at reduced pressure. The residue is purified by FCC (EtOAc/AcOH/H$_2$O 6:1:1) to afford the title compound as an orange powder. $^1$H NMR (d$_6$-DMSO 400 MHz): δ 2.05 (s, 3H), 2.04-2.11 (m, 4H), 2.46 (s, 3H), 3.06-3.14 (m, 4H), 6.35 (d, J=8.1 Hz, 1H), 6.65 (dd, J=8.1, 7.2 Hz, 1H), 6.84 (d, J=7.2 Hz, 1H), 6.87 (d, J=2.0 Hz,1H), 7.95 (s, 1H), 8.16 (d, J=2.0 Hz, 1H). ES$^+$–MS: 447 [M+H]$^+$.

Preparation of 2-[5-(4-Methyl-piperazin-1-yl)-2-nitro-pyridin-3-yl]-acetamide

A solution of [5-(4-Methyl-piperazin-1-yl)-2-nitro-pyridin-3-yl]-acetic acid methyl ester (222 mg, 0.75 mmol) in 33% aq. NH$_4$OH (100 mL) is stirred for 16 h at 50° C. in a sealed autoclave. TLC analysis indicated complete consumption of starting material. The solvent is evaporated at reduced pressure to afford the title compound as a yellow solid in a 3:2 mixture with the corresponding carboxylic acid. $^1$H NMR (d$_6$-DMSO 400 MHz): δ 2.18 (s, 3H), 2.36-2.44 (m, 4H), 3.36-3.44 (m, 4H), 3.77 (s, 2H), 6.92 (bs, 1H), 7.34 (d, J=2 Hz, 1H), 7.44 (bs, 1H), 8.07 (d, J=2 Hz, 1H). ES$^+$–MS: 280.4 [M+H]$^+$.

Preparation of [5-(4-Methyl-piperazin-1-yl)-2-nitro-pyridin-3-yl]-acetic acid methyl ester A mixture of (5-Bromo-2-nitro-pyridin-3-yl)-acetic acid methyl ester (472 mg, 1.72 mmol) and N-methylpiperazine (344 mg, 3.44 mmol) is heated for 18 h under an argon atmosphere. TLC analysis indicated complete consumption of starting material. The reaction mixture is cooled to RT, diluted with water and adjusted to pH 8-9 with a saturated aq. NaHCO$_3$ solution. The aqueous phase is extracted three times with methylene chloride and the combined organic layers are washed with brine, dried over Na$_2$SO$_4$, and concentrated at reduced pressure. The crude product is purified by FCC (methylene chloride/MeOH 95:5 to 90:10) to afford the title compound as a yellow solid. $^1$H NMR (d$_6$-DMSO 400 MHz): δ 2.01 (s, 3H), 2.22-2.26 (m, 4H), 3.24-3.28 (m, 4H), 3.40 (s, 3H), 3.81 (s, 2H), 7.26 (d, J=2 Hz, 1H), 7.97 (d, J=2 Hz, 1H). ES$^+$–MS: 295.3 [M+H]$^+$.

Preparation of (5-Bromo-2-nitro-pyridin-3-yl)-acetic acid methyl ester

To a suspension of 5-Bromo-2-nitro-pyridine (2.33 g, 11.5 mmol) and trimethylsilanyl-acetic acid methyl ester (1.8 g, 12.0 mmol) in THF (12 mL) is added at −78° C. a solution of dried TBAF (3.0 g, 11.5 mmol), obtained by drying TBAF×3 H$_2$O (7.5 g) for 18 h at 70° C. under high vacuum, in a mixture of acetonitrile (6 mL) and THF (6 mL). The resulting deep red solution is stirred for 1 h at −40° C. TLC analysis indicated complete consumption of starting material. The reaction mixture is cooled to −78° C. and DDQ (2.6 g, 11.5 mmol) is carefully added. The black solution is slowly warmed to RT. Since TLC analysis indicated that no further changes occurred, the reaction mixture is partitioned between EtOAc and a saturated aq. NH$_4$Cl solution. The layers are separated and the organic layer is washed with a saturated aqueous NH$_4$Cl solution, brine, dried over Na$_2$SO$_4$ and concentrated at reduced pressure. The crude product is purified by FCC (cyclohexane/EtOAc 9:1 to 8:1) to afford the title compound as yellow needles. $^1$H NMR (CDCl$_3$, 400 MHz): δ 3.94 (s, 3H), 4.17 (s, 2H), 8.20 (s, 1H), 8.78 (s, 1H).

By following the procedures of Examples 28 and 29, but using the appropriate starting materials, the compounds of formula E wherein R$_a$, R$_b$, and R$_2$ are as indicated in Table 6 below, may be obtained.

TABLE 6

[Structure E: pyrrole-2,5-dione core with pyridine bearing R₂ and N-methylpiperazine substituent, and indole bearing Rₐ (on N) and Rᵦ]

| | R₂ | Rₐ | Rᵦ | MS |
|---|---|---|---|---|
| 30 | H | CH₃ | H | MH⁺ 402 |
| 31 | H | H | H | MH⁺ 388 |
| 32 | CF₃ | H | CH₃ | MH⁺ 470 |
| 33 | CF₃ | H | H | MH⁺ 456 |
| 34 | CF₃ | CH₃ | H | MH⁺ 470 |
| 35 | H | H | CH₃ | MH⁺ 402 |
| 36 | NO₂ | H | H | MH⁺ 433 |
| 37 | Cl | H | CH₃ | MH⁺ 437 |

EXAMPLE 38

3-(7-Methyl-1H-indol-3-yl)-4-[2-(4-methyl-piperazin-1-yl)-pyridin-4-yl]-pyrrole-2,5-dione

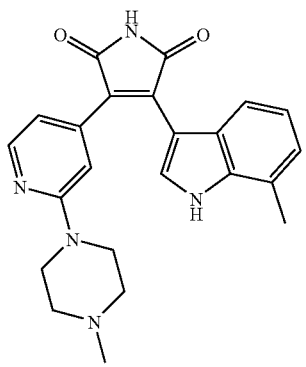

A mixture of ²-[2-(4-Methyl-piperazin-1-yl)-pyridin-4-yl]-acetamide (34 mg, 0.15 mmol) and (7-methyl-1H-indol-3-yl)-oxo-acetic acid methyl ester (47 mg, 0.22 mmol) is azeotropically dried by dissolving in dry THF (3 ml) and evaporation. Under an atmosphere of argon, the mixture is dissolved in dry THF (1 ml), and a solution of 1.0 M KOtBu in THF (0.44 ml, 0.44 mmol) is added dropwise at RT. After 5 minutes at RT, TLC analysis indicated complete conversion of starting materials. The reaction mixture is diluted with EtOAc and poured into a saturated aqueous NH₄Cl solution. The organic layer is separated, washed with brine, dried over Na₂SO₄, and the organic layer is evaporated. The residue is purified by FCC (CH₂Cl₂/MeOH 95:5 to 90:10 to 85:15) and by preparative HPLC (H₂O/MeCN/TFA 95:5:0.1) to afford the title compound as a red TFA salt. ¹H NMR (d₆-DMSO, 400 MHz): δ 2.48 (s, 3H), 2.78 (s, 3H), 2.78-3.02 (m, 4H), 3.39 (d, J=12 Hz, 2H), 4.14 (d, J=13 Hz, 2H), 6.24 (d, J=9 Hz, 1H), 6.71 (d, J=6 Hz, 1H), 8.03 (d, J=3 Hz, 1H), 8.10 (d, J=6 Hz, 1H), 9.71 (s, broad, 1H), 11.19 (s, 1H), 12.09 (d, J=3 Hz, 1H). ES⁺–MS: 402.5 [M+H]⁺, ES⁻–MS: 400.3 [M–H]⁻.

Preparation of 2-[2-(4-Methyl-piperazin-1-yl)-pyridin-4-yl]-acetamide

[2-(4-Methyl-piperazin-1-yl)-pyridin-4-yl]-acetic acid tert-butyl ester (95 mg, 0.33 mmol) is dissolved in a mixture of TFA and CH₂Cl₂ (5 ml/5 ml) and stirred at RT. After 1 h at RT, TLC analysis indicated complete conversion of starting material. The solvent is removed by rotary evaporation, and replaced by dry DMF (1.5 ml). Under an atmosphere of argon, carbonyl diimidazole (58 mg, 0.36 mmol) is added. After 20 minutes at RT, TLC analysis indicated complete conversion of the carboxylic acid. An aqueous solution of ammonia (25%, 6 ml) is added at RT. After 15 minutes at RT, solvents are removed under high vacuum. The residue is dissolved in CH₂Cl₂/MeOH (9:1) and purified by FCC (CH₂Cl₂/MeOH, slow gradient from 95:5 to 40:60) to yield the title compound. ¹H NMR (d₄-MeOD, 400 MHz): δ 2.35 (s, 3H), 2.56 (m, 4H), 3.46 (s, 2H), 3.54 (m, 4H), 6.66 (d, J=6 Hz, 1H), 6.78 (s, 1H), 8.02 (d, J=6 Hz, 1H). ES⁺–MS: 235.3 [M+H]⁺.

Preparation of [2-(4-Methyl-piperazin-1-yl)-pyridin-4-yl]-acetic acid tert-butyl ester Potassium phosphate (2.65 g, 12.47 mmol) is dried at 120° C. under high vacuum for 45 minutes. After cooling to RT and venting with dry argon, palladium dibenzylideneacetone (Pd₂(dba)₃, 25 mg, 0.03 mmol) and di-tert-butylphosphino pentaphenylferrocene (39 mg, 0.06 mmol) are added. (2-Chloro-pyridin-4-yl)-acetic acid tert-butyl ester (631 mg, 2.77 mmol), dissolved in 1,2-dimethoxyethane (14 ml, dried by passing through a column of basic aluminum oxide), and 1-methyl piperazine (830 mg, 8.31 mmol) are added. The reaction mixture is warmed to 40° C. for 1 h. Additional Pd₂(dba)₃ (25 mg, 0.03 mmol) and phosphine ligand (39 mg, 0.06 mmol) is added, and stirring is continued at 60° C. for 2 h. Additional Pd₂(dba)₃ (25 mg, 0.03 mmol) and phosphine ligand (39 mg, 0.06 mmol) is added, and stirring is continued at 90° C. for 18 h and at RT for 72 h. TLC and MS analysis indicated the presence of desired product. The reaction mixture is diluted with EtOAc and poured into a saturated solution of NaCl in water. The organic layer is separated, dried over Na₂SO₄, and the solvent is evaporated. Purification of the residue by FCC (hexane/EtOAc, gradient from 95:5 to 90:10) affords the title compound. ¹H NMR (CDCl₃, 400 MHz): δ 1.44 (s, 9H), 2.34 (s, 3H), 2.52 (m, 4H), 3.42 (s, 2H), 3.55 (m, 4H), 6.55 (d, J=4 Hz, 1H), 6.56 (s, 1H), 8.11 (d, J=4 Hz, 1H). ES⁺–MS: 292.4 [M+H]⁺.

Preparation of (2-Chloro-pyridin-4-yl)-acetic acid tert-butyl ester

Hexamethyl disilazane (5.45 g, 33.8 mmol) is dissolved in dry toluene (80 ml) under an atmosphere of argon. After thoroughly purging the solvent with argon, the solution is cooled to −78° C., and n-BuLi (21.1 ml of a 1.6 M solution in hexanes, 33.8 mmol) is added. The mixture is stirred for 15 minutes at −78° C. and for 15 minutes at RT, whereupon a clear solution is obtained. Palladium dibenzylideneacetone (Pd₂(dba)₃, 743 mg, 0.81 mmol) and (2′-dicyclohexylphosphanyl-biphenyl-2-yl)-dimethyl-amine (670 mg, 1.70 mmol) are added. The mixture is stirred for 10 minutes at RT, then it is cooled to −10° C. Acetic acid tert-butyl ester (3.61 g, 31.08 mmol) is slowly added neat. After 10 minutes at −10° C., 2,4-dichloropyridine (4.00 g, 27.03 mmol) is added in one portion. The reaction mixture is allowed to warm to RT. After 1 h, TLC analysis indicated complete consumption of starting materials. The reaction mixture is diluted with EtOAc and poured into a saturated aqueous NH$_4$Cl solution. The organic layer is separated, washed with brine, dried over Na$_2$SO$_4$, and the solvent is evaporated. The residue is purified by FCC (hexanes/EtOAc, gradient from 97:3 to 90:10) to afford the title compound. $^1$H NMR (CDCl$_3$, 400 MHz): δ 1.44 (s, 9H), 3.51 (s, 2H), 7.15 (dd, J=1 Hz, 4 Hz, 1H), 7.27 (d, J=1 Hz, 1H), 8.32 (d, J=4 Hz). ES$^+$–MS: 228.2, 230.1 (Cl) [M+H]$^+$.

EXAMPLE 39

3-(7-Methyl-1H-indol-3-yl)-4-[5-methyl-2-(4-methyl-piperazin-1-yl)-pyridin-4-yl]-pyrrole-2,5-dione

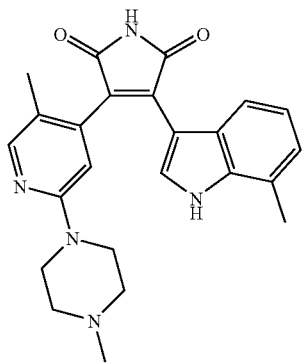

A mixture of 2-[5-methyl-2-(4-methyl-piperazin-1-yl)-pyridin-4-yl]-acetamide (30 mg, 0.12 mmol) and (7-methyl-1H-indol-3-yl)-oxo-acetic acid methyl ester (39 mg, 0.18 mmol) is azeotropically dried by dissolving in dry THF (3 ml) and evaporation. Under an atmosphere of argon, the mixture is dissolved in dry THF (1 ml), and a solution of 1.0 M KOtBu in THF (0.36 ml, 0.36 mmol) is added dropwise at RT. After 10 minutes at RT, TLC analysis indicated complete conversion of starting materials. The reaction mixture is diluted with EtOAc and poured into a saturated aqueous NH$_4$Cl solution. The organic layer is separated, washed with brine, dried over Na$_2$SO$_4$, and the organic layer is evaporated. The residue is purified by preparative HPLC (H$_2$O/MeCN/TFA 95:5:0.1) to afford the title compound as a red TFA salt. $^1$H NMR (d$_6$-DMSO, 400 MHz): δ 1.79 (s, 3H), 2.44 (s, 3H), 2.79 (d, J=3 Hz, 3H), 2.75-3.07 (m, 2H), 3.44 (s, broad, 2H), 4.25 (s, broad, 2H), 6.30 (d, J=8 Hz, 1H), 6.64 (dd, J=8 Hz, 8 Hz, 1H), 6.86 (s, 1H), 6.88 (d, J=8 Hz, 1H), 8.00 (d, J=2 Hz, 1H), 8.04 (s, 1H), 9.70 (s, broad, 1H), 11.16 (s, 1H), 12.04 (d, J=2 Hz, 1H). $^{19}$F NMR (d$_6$-DMSO, 400 MHz): δ −74.542. ES$^+$–MS: 416.4 [M+H]$^+$, ES$^-$–MS: 414.4 [M–H]$^-$.

Preparation of 2-[5-methyl-2-(4-methyl-piperazin-1-yl)-pyridin-4-yl]-acetamide

[5-Methyl-2-(4-methyl-piperazin-1-yl)-pyridin-4-yl]-acetic acid tert-butyl ester (320 mg, 1.05 mmol) is dissolved in a mixture of TFA and CH$_2$Cl$_2$ (10 ml/10 ml) and stirred at RT. After 1 h at RT, TLC analysis indicated complete conversion of starting material. The solvent is removed by rotary evaporation, and replaced by dry DMF (1.5 ml). Under an atmosphere of argon, carbonyl diimidazole (187 mg, 1.16 mmol) is added. After 30 minutes at RT, TLC analysis indicated complete conversion of the carboxylic acid. An aqueous solution of ammonia (25%, 16 ml) is added at RT. After 15 minutes at RT, solvents are removed under high vacuum. The residue is dissolved in CH$_2$Cl$_2$/MeOH (9:1) and purified by FCC (CH$_2$Cl$_2$/MeOH, slow gradient from 95:5 to 40:60) to yield the title compound. $^1$H NMR (d$_6$-DMSO, 400 MHz): δ 2.07 (s, 3H), 2.38 (s, 3H), 2.64 (s, broad, 4H), 3.34 (s, 2H), 3.46 (s, broad, 4H), 6.72 (s, 1H), 6.95 (s, broad, 1H), 7.44 (s, broad, 1H), 7.87 (s, 1H). ES$^+$–MS: 249.3 [M+H]$^+$, ES$^-$–MS: 247.3 [M–H]$^-$.

Preparation of [5-Methyl-2-(4-methyl-piperazin-1-yl)-pyridin-4-yl]-acetic acid tert-butyl ester Sodium tert-butoxide (227 mg, 2.37 mmol) is dried under high vacuum at approximately 80° C. After purging with argon and cooling to RT, palladium acetate (39 mg, 0.17 mmol), rac-2,2'-bis-diphenylphosphanyl-[1,1']binaphthalenyl (rac-BINAP, 54 mg, 0.09 mmol) and (2-chloro-5-methyl-pyridin-4-yl)-acetic acid tert-butyl ester (520 mg, 2.15 mmol) are added. The mixture is dissolved in dioxane (7 ml, degassed with three freeze-thaw cycles under HV/argon), and 1-methyl-piperazine (237 mg, 2.37 mmol) is added. The round bottom flask containing the reaction mixture is immersed into a pre-heated oil bath (T=85° C.). After 30 minutes, TLC analysis indicated almost complete conversion of starting materials. The reaction mixture is diluted with EtOAc and poured into a saturated aqueous NH$_4$Cl solution. The organic layer is separated, washed with brine, dried over Na$_2$SO$_4$, and the solvent is evaporated. The residue is purified by FCC (CH$_2$Cl$_2$/MeOH, slow gradient from 98:2 to 90:10) to afford the title compound. $^1$H NMR (CDCl$_3$, 400 MHz): δ 1.43 (s, 9H), 2.14 (s, 3H), 2.34 (s, 3H), 2.51 (m, 4H), 3.44 (s, 2H), 3.49 (m, 4H), 6.51 (s, 1H), 7.96 (s, 1H). ES$^+$–MS: 306.4 [M+H]$^+$.

Preparation of (2-chloro-5-methyl-pyridin-4-yl)-acetic acid tert-butyl ester

Hexamethyl disilazane (1.33 g, 8.23 mmol) is dissolved in dry toluene (15 ml) under an atmosphere of argon. After thoroughly purging the solvent with argon, the solution is cooled to −78° C., and n-BuLi (5.1 ml of a 1.6 M solution in hexanes, 8.23 mmol) is added. The mixture is stirred for 15 minutes at −78° C. and for 15 minutes at rt, whereupon a clear solution is obtained. Palladium dibenzylideneacetone (Pd$_2$(dba)$_3$, 151 mg, 0.16 mmol) and (2'-dicyclohexylphosphanyl-biphenyl-2-yl)-dimethyl-amine (136 mg, 0.35 mmol) are added. The mixture is stirred for 10 minutes at RT, then it is cooled to −10° C. Acetic acid tert-butyl ester (924 mg, 7.96 mmol) is slowly added heat. After 10 minutes at −10° C., 2,4-dichloro-5-methyl-pyridine (889 mg, 5.49 mmol) is added in one portion. The reaction mixture is allowed to warm to RT. After 1 h, TLC analysis indicated complete consumption of starting materials. The reaction mixture is diluted with EtOAc and poured into a saturated aqueous NH$_4$Cl solution. The organic layer is separated, washed with brine, dried over Na$_2$SO$_4$, and the solvent is evaporated. The residue is purified by FCC (hexanes/EtOAc, gradient from 100:0 to 90:10) to afford the title compound. $^1$H NMR (CDCl$_3$, 400 MHz): δ

1.45 (s, 9H), 2.26 (s, 3H), 3.52 (s, 2H), 7.18 (s, 1H), 8.18 (s, 1H). ES+–MS: 242.2, 244.2 (Cl) [M+H]+.

Preparation of 2,4-dichloro-5-methyl-pyridine 2,4-Dichloro-5-chloromethyl-pyridine (1.43 g, 7.28 mmol) is dissolved in ethanol (14 ml). After addition of triethyl amine (737 mg, 7.28 mmol), Raney nickel (143 mg) is added. The reaction vessel is connected to a balloon filled with H2. After 3 hours of very vigorous magnetically stirring at RT, NMR analysis of a reaction aliquot indicated complete conversion of the starting material. The reaction mixture is diluted with EtOAc and poured into water.

The aqueous layer is extracted three times with EtOAc. The combined organic layers are dried over Na$_2$SO$_4$. Careful removal of the solvent yields the title compound of adequate purity for further use. $^1$H NMR (CDCl$_3$, 400 MHz): δ 2.33 (s, 3H), 7.35 (s, 1H), 8.23 (s, 1H). ES+–MS: 160, 162, 164 (2 Cl) [M+H]+.

Preparation of 2,4-Dichloro-5-chloromethyl-pyridine (4,6-Dichloro-pyridin-3-yl)-methanol (2.21 g, 12.41 mmol) is cooled under an atmosphere of argon to 0° C. Thionyl chloride (8 ml) is carefully added. After 5 minutes at 0° C., the solution is heated to reflux. After 10 minutes, TLC analysis indicated complete conversion of the starting material. After cooling to RT, excess thionyl chloride is removed via a membrane pump. The remaining oil is dissolved in EtOAc. The solution is poured into a concentrated aqueous solution of NaHCO$_3$. The organic layer is separated and washed twice with a concentrated aqueous solution of NaCl. After drying over Na$_2$SO$_4$, the organic solvent is removed to afford the title compound of adequate purity for immediate further use. $^1$H NMR (CDCl$_3$, 400 MHz): δ 4.65 (s, 2H), 7.42 (s, 1H), 8.44 (s,1H). ES+–MS: 195, 197, 199 (3 Cl) [M+H]+.

Preparation of 2(4,6-Dichloro-pyridin-3-yl)-methanol 4,6-Dichloro-nicotinic acid ethyl ester (5.0 g, 22.72 mmol) is dissolved in dioxane (30 ml). A solution of lithium hydroxide (599 mg, 24.99 mmol) in water (20 ml) is added, and the mixture is stirred at RT. After 30 minutes, TLC analysis indicated complete conversion of the starting material. The solvents are removed, and the residual lithium salt of 4,6-dichloro-nicotinic acid, after thorough drying under high vacuum, is used directly in the next step. $^1$H NMR (d$_6$-DMSO, 400 MHz): δ 7.54 (s, 1H), 8.34 (s, 1H). ES−–MS: 190.1, 192.1, 194.1 (2 Cl) [M–H]−.

The lithium salt of 4,6-dichloro-nicotinic acid (4.5 g, 22.72 mmol) is suspended in thionyl chloride (28 ml) under an atmosphere of argon. After homogenizing the mixture in an ultrasonic bath, the reaction mixture is heated to reflux for 2.5 h, after which TLC analysis indicated complete consumption of the starting material. The solution is cooled to RT, and excess thionyl chloride is removed with a membrane pump. The solid residue is cooled to 0° C., and a solution of sodium borohydride (3.10 g, 81.85 mmol) in water (35 ml) is very carefully added. After 1 h at RT, TLC analysis indicated complete conversion. The reaction mixture is diluted with EtOAc, and the aqueous layer is saturated with NaCl. The organic layer separated, washed with brine, dried over Na$_2$SO$_4$ and the solvent is removed. Purification by FCC (hexanes:EtOAc, gradient from 9:1 to 7:3) affords the title compound. $^1$H NMR (CDCl$_3$, 400 MHz): δ 2.00 (t, J=6 Hz, 1H), 4.81 (d, J=6 Hz, 2H), 7.38 (s, 1H), 8.47 (s, 1H). ES+–MS: 178.1, 180.1, 181.9 (2 Cl) [M+H]+.

By following the procedure of Example 39, but using the appropriate starting materials, the compounds of formula F wherein R$_c$, R$_d$, R$_a$, are H; and R$_a$ and R$_b$ are as indicated in Table 7 below, may be obtained.

TABLE 7

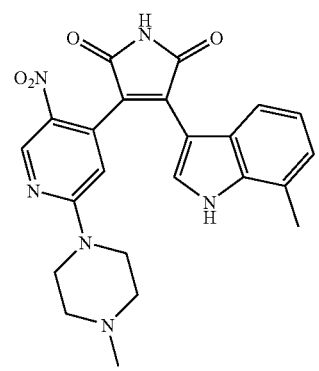

F

| | R$_a$ | R$_b$ | MS |
|---|---|---|---|
| 40 | H | H | MH+ 402 |

EXAMPLE 41

3-(7-Methyl-1H-indol-3-yl)-4-[2-(4-methyl-piperazin-1-yl)-5-nitro-pyridin-4-yl]-pyrrole-2,5-dione A mixture of 2-[2-(4-Methyl-piperazin-1-yl)-5-nitro-pyridin-4-yl]-acetamide (50 mg, 0.18 mmol) and (7-methyl-1H-indol-3-yl)-oxo-acetic acid methyl ester (60 mg, 0.27 mmol) is azeotropically dried by dissolving in dry THF (10 ml) and evaporation. Under an atmosphere of argon, the mixture is dissolved in dry THF (3 ml), and a solution of 1.0 M KOtBu in THF (0.54 ml, 0.54 mmol) is added dropwise at RT. After 10 minutes at RT, TLC analysis indicated complete conversion of starting materials. The reaction mixture is diluted with EtOAc and poured into a saturated aqueous NH$_4$Cl solution. The organic layer is separated, washed with brine, dried over Na$_2$SO$_4$, and the organic layer is evaporated. The residue is purified by preparative HPLC (H$_2$O/MeCN/TFA 95:5:0.1) to afford the title compound as a red TFA salt. $^1$H NMR (d$_6$-DMSO, 400 MHz): δ 2.48 (s, 3H), 2.70 (s, 3H), 3.00-3.22 (s, broad, 1H), 4.05-4.43 (s, broad, 4H), 6.44 (d, J=8 Hz, 1H), 6.64 (s, 1H), 6.76 (dd, J=8 Hz, 8 Hz, 1H), 6.92 (d, J=8 Hz, 1H), 8.05 (d, J=2 Hz, 1H), 9.07 (s, 1H), 9.80 (s, broad, 1H), 11.30 (s, 1H), 12.10 (d, J=2 Hz, 1H). $^{19}$F NMR (d$_6$-DMSO, 400 MHz): δ −73.959. ES$^+$−MS: 447.3 [M+H]$^+$, ES$^-$−MS: 445.3 [M−H]$^-$.

Preparation of 2-[2-(4-Methyl-piperazin-1-yl)-5-nitro-pyridin-4-yl]-acetamide

[2-(4-Methyl-piperazin-1-yl)-5-nitro-pyridin-4-yl]-acetic acid ethyl ester (250 mg, 0.81 mmol) is dissolved in methanol (2.5 ml). An aqueous solution of ammonia (25%, 2.5 ml) is added, and the mixture is warmed to 40° C. for 18 h. TLC analysis indicated complete conversion of the starting material. Solvents are removed, and the residue is purified by FCC (CH$_2$Cl$_2$/MeOH, gradient from 97:3 to 90:10) to afford the title compound. $^1$H NMR (d$_6$-DMSO, 400 MHz): δ 2.21 (s, 3H), 2.38 (m, 4H), 3.72 (m, 4H), 3.80 (s, 2H), 6.84 (s, 1H), 6.93 (s, broad, 1H), 7.46 (s, broad, 1H), 8.85 (s, 1H). ES$^+$−MS: 280.3 [M+H]$^+$, ES$^-$−MS: 278.3 [M−H]$^-$.

Preparation of [2-(4-Methyl-piperazin-1-yl)-5-nitro-pyridin-4-yl]-acetic acid ethyl ester Potassium phosphate (2.48 g, 11.67 mmol) is dried at 120° C. under high vacuum for 45 minutes. After cooling to RT and venting with dry argon, palladium dibenzylideneacetone (Pd$_2$(dba)$_3$, 24 mg, 0.026 mmol) and di-tert-butylphosphino pentaphenylferrocene (37 mg, 0.052 mmol) are added. (2-Bromo-5-nitro-pyridin-4-yl)-acetic acid ethyl ester (750 mg, 2.59 mmol), dissolved in 1,2-dimethoxyethane (10 ml, dried by passing through a column of basic aluminium oxide), and 1-methyl piperazine (780 mg, 7.78 mmol) are added. The reaction mixture is stirred at RT for 10 minutes, after which TLC and MS analysis indicated complete conversion of the starting material. The reaction mixture is diluted with EtOAc and poured into a saturated solution of NaCl in water. The organic layer is separated, dried over Na$_2$SO$_4$, and the solvent is evaporated. Purification of the residue by FCC (hexane/EtOAc, gradient from 95:5 to 90:10) affords the title compound. $^1$H NMR (CDCl$_3$, 400 MHz): δ 1.26 (t, J=7 Hz, 3H), 2.35 (s, 3H), 2.50 (m, 4H), 3.76 (m, 4H), 3.94 (s, 2H), 4.18 (q, J=7 Hz, 2H), 6.36 (s, 1H), 9.05 (s, 1H). ES$^+$−MS: 309.3 [M+H]$^+$, ES$^-$−MS: 307.3 [M−H]$^-$.

Preparation of (2-Bromo-5-nitro-pyridin-4-yl)-acetic acid ethyl ester

2-Bromo-5-nitropyridine (1.84 g, 9.06 mmol) and trimethylsilanyl-acetic acid ethyl ester (1.53 g, 9.52 mmol) are dissolved under an atmosphere of argon in dry THF (10 ml). After cooling to −78° C., a solution of tetrabutylammonium fluoride (TBAF, 2.37 g, vacuum-dried overnight) in a mixture of THF and acetonitrile (10 ml/10 ml) is slowly added, so that the reaction temperature did not rise above −65° C. After complete addition, the mixture is stirred at −40° C. for 30 minutes, and at −20° C. for 10 minutes. The reaction mixture is re-cooled to −78° C., and 2,3-dichloro-5,6-dicyano-p-benzochinone (DDQ, 2.06 g, 9.06 mmol) is added. The suspension is allowed to warm to RT. TLC analysis indicated complete conversion. The reaction mixture is diluted with EtOAc and poured into a saturated solution of NH$_4$Cl solution. The organic layer is separated, washed with brine, dried over Na$_2$SO$_4$, and the solvent is evaporated. The residue is purified by FCC (toluene/EtOAc 100:0 to 97:3) to afford the title compound. $^1$H NMR (CDCl$_3$, 400 MHz): δ 1.26 (t, J=7 Hz, 3H), 4.01 (s, 2H), 4.19 (q, J=7 Hz, 2H), 7.53 (s, 1H), 9.06 (s, 1H). ES$^-$−MS: 287, 289 [M−H]$^-$.

By following the procedure of Example 41, but using the appropriate starting materials, the compounds of formula G wherein R$_a$ and R$_b$ are as indicated in Table 8 below, may be obtained.

TABLE 8

G

| | R$_a$ | R$_b$ | MS |
|---|---|---|---|
| 42 | H | H | MH$^+$ 433 |

EXAMPLE 43

3-[5-Chloro-2-(4-methyl-piperazin-1-yl)-pyridin-4-yl]-4-(7-methyl-1H-indol-3-yl)-pyrrole-2,5-dione

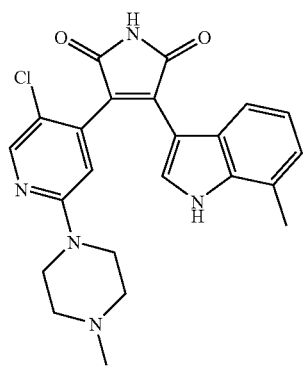

A mixture of 2-[5-Chloro-2-(4-methyl-piperazin-1-yl)-pyridin-4-yl]-acetamide (90 mg, 0.18 mmol) and (7-methyl-1H-indol-3-yl)-oxo-acetic acid methyl ester (109 mg, 0.50 mmol) is azeotropically dried by dissolving in dry THF (10 ml) and evaporation. Under an atmosphere of argon, the mixture is dissolved in dry THF (3 ml), and a solution of 1.0 M KOtBu in THF (1.0 ml, 1.0 mmol) is added dropwise at RT. After 10 minutes at RT, TLC analysis indicated complete conversion of starting materials. The reaction mixture is diluted with EtOAc and poured into a saturated aqueous NH$_4$Cl solution. The organic layer is separated, ished with brine, dried over Na$_2$SO$_4$, and the organic layer is evaporated. The residue is purified by preparative HPLC (H$_2$O/MeCN/TFA 95:5:0.1) to afford the title compound as a red TFA salt. $^1$H NMR (d$_6$-DMSO, 400 MHz): δ 2.45 (s, 3H), 2.78 (s, 3H), 2.82-3.13 (m, 4H), 4.27 (m, 2H), 6.40 (d, J=8 Hz, 1H), 6.70 (dd, J=7 Hz, 8 Hz, 1H), 6.90 (d, J=7 Hz, 1H), 7.00 (s, 1H), 8.03 (d, J=2 Hz, 1H), 8.26 (s, 1H), 9.74 (s, broad, 1H), 11.27 (s, 1H), 12.1 (d, J=2 Hz, 1H). ES⁺-MS: 436.3 [M+H]⁺, ES⁻-MS: 434.3 [M-H]⁻.

Preparation of 2-[5-Chloro-2-(4-methyl-piperazin-1-yl)-pyridin-4-yl]-acetamide

[5-Chloro-2-(4-methyl-piperazin-1-yl)-pyridin-4-yl]-acetic acid ethyl ester (385 mg, 1.29 mmol) is dissolved under an atmosphere of argon in dry DMF (4 ml). Formamide (195 mg, 4.33 mmol) is added, and the mixture is heated to 105° C. At this temperature, sodium methoxide (5.4 M in MeOH, 0.24 ml, 1.29 mmol) is added dropwise. After 20 minutes, TLC analysis indicated incomplete conversion, thus another addition of sodium methoxide (0.08 ml of a 5.4 M solution in MeOH) is done. After a further 10 minutes, the reaction is judged complete according to TLC. The reaction mixture is cooled to RT and diluted with CH₂Cl₂ (150 ml). Water is added (3 ml) until a clear solution is obtained. Sufficient Na₂SO₄ is added to absorb the water and the organic solvent is evaporated. The residue is purified by FCC (CH₂Cl₂/MeOH 95:5 to 80:20) to afford the title compound. ¹H NMR (CDCl₃, 400 MHz): δ 2.35 (s, 3H), 2.51 (m, 4H), 3.56 (m, 4H), 3.62 (s, 2H), 5.37 (s, broad, 1H), 5.54 (s, broad, 1H), 6.64 (s, 1H), 8.15 (s, 1H). ES⁺-MS: 269.2, 271.1 (Cl) [M+H]⁺, ES⁻-MS: 267.2, 269.3 (Cl) [M-H]⁻.

Preparation of [5-Chloro-2-(4-methyl-piperazin-1-yl)-pyridin-4-yl]-acetic acid ethyl ester

[5-Amino-2-(4-methyl-piperazin-1-yl)-pyridin-4-yl]-acetic acid ethyl ester (680 mg, 2.44 mmol) is dissolved under an atmosphere of argon in 18% aqueous hydrochloric acid (12 ml). After cooling the solution to 0° C., a solution of sodium nitrite (244 mg, 3.54 mmol) in water (6 ml) is added over 15 minutes, taking care that the internal temperature did not rise above 5° C. After 20 minutes at 0° C., the reaction mixture is added to a −10° C. solution of copper(I) chloride (freshly prepared, 725 mg, 7.33 mmol) in water (1.8 ml). After 15 minutes at −10° C., TLC analysis indicated complete conversion. The reaction mixture is diluted with EtOAc and poured in a saturated aqueous NaCl solution. The organic layer is separated, dried over Na₂SO₄, and concentrated. The residue is purified by FCC (CH₂Cl₂/MeOH, gradient from 98:2 to 90:10) to afford the title compound. ¹H NMR (CDCl₃, 400 MHz): δ 1.27 (t, J=7 Hz, 3H), 2.34 (s, 3H), 2.50 (m, 4H), 3.52 (m, 4H), 3.66 (s, 2H), 4.19 (q, J=7 Hz, 2H), 6.59 (s, 1H), 8.11 (s, 1H). ES⁺-MS: 298.2, 300.1 (Cl) [M+H]⁺, ES⁻-MS: 296.2, 298.2 (Cl) [M-H]⁻.

Preparation of [5-Amino-2-(4-methyl-piperazin-1-yl)-pyridin-4-yl]-acetic acid ethyl ester

[2-(4-Methyl-piperazin-1-yl)-5-nitro-pyridin-4-yl]-acetic acid ethyl ester (2.78 g, 9.02 mmol) is dissolved in MeOH (28 ml). Palladium on carbon (10%, 96 mg, 0.90 mmol) is added, and the reaction flask is connected to a balloon filled with hydrogen. After vigorous stirring for 2.5 h, TLC analysis indicated complete conversion. The reaction mixture is filtered, the organic solvent removed, and the residue purified by FCC (CH₂Cl₂/MeOH, gradient from 97:3 to 70:30) to yield [5-amino-2-(4-methyl-piperazin-1-yl)-pyridin-4-yl]-acetic acid ethyl ester. ¹H NMR (CDCl₃, 400 MHz): δ 1.27 (t, J=7 Hz, 3H), 2.35 (s, 3H), 2.54 (m, 4H), 3.40 (m, 4H), 3.55 (s, 2H), 3.62 (s, broad, 2H), 4.16 (q, J=7 Hz, 2H), 6.50 (s, 1H), 7.79 (s, 1H). ES⁺-MS: 279.3 [M+H]⁺.

By following the procedure of Example 43, but using the appropriate starting materials, the compounds of formula H wherein R_a and R_b are as indicated in Table 9 below, may be obtained.

TABLE 9

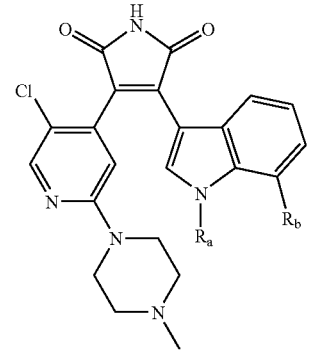

H

| | R_a | R_b | MS |
|---|---|---|---|
| 44 | H | H | MH⁺ 422, 423 |

EXAMPLE 45

3-(7-Methyl-1H-indol-3-yl)-4-[2-(4-methyl-piperazin-1-yl)-5-trifluoromethyl-pyridin-4-yl]-pyrrole-2,5-dione

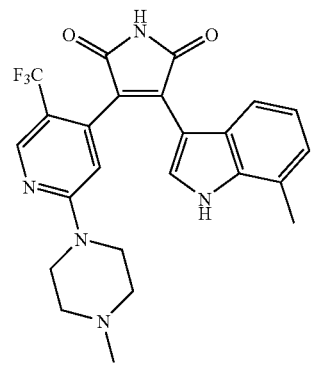

A mixture of 2-[2-(4-Methyl-piperazin-1-yl)-5-trifluoromethyl-pyridin-4-yl]-acetamide (80 mg, 0.26 mmol) and (7-methyl-1H-indol-3-yl)-oxo-acetic acid methyl ester (86 mg, 0.40 mmol) is azeotropically dried by dissolving in dry THF (10 ml) and evaporation. Under an atmosphere of argon, the mixture is dissolved in dry THF (3 ml), and a solution of 1.0 M KOtBu in THF (1.05 ml, 1.05 mmol) is added dropwise at RT. After 45 minutes at RT, TLC analysis indicated complete conversion of starting materials. The reaction mixture is diluted with EtOAc and poured into a saturated aqueous NH₄Cl solution. The organic layer is separated, washed with brine, dried over Na₂SO₄, and the organic layer is evaporated. The residue is purified by preparative HPLC (H₂O/MeCN/TFA 95:5:0.1) to afford the title compound as a red TFA salt. ¹H NMR (d₆-DMSO, 400 MHz): δ 2.44 (s, 3H), 2.78 (s, 3H), 2.74-3.54 (m, broad, 6H), 4.34-4.58 (m, broad, 2H), 6.62 (d, J=8 Hz, 1H), 6.74 (dd, J=7 Hz, 8 Hz, 1H), 6.90 (d, J=7 Hz, 1H), 7.03 (s, 1H), 7.96 (d, J=3 Hz, 1H), 8.58 (s, 1H), 9.84 (s, broad, 1H), 11.27 (s, 1H), 12.01 (d, J=3 Hz, 1H). $^{19}$F NMR (d$_6$-DMSO, 400 MHz): δ −74.00, −57.33. ES$^+$−MS: 470.3 [M+H]$^+$.

Preparation of 2-[2-(4-Methyl-piperazin-1-yl)-5-trifluoromethyl-pyridin-4-yl]-acetamide

[2-(4-Methyl-piperazin-1-yl)-5-trifluoromethyl-pyridin-4-yl]-acetic acid tert-butyl ester (475 mg, 1.32 mmol) is dissolved in a mixture of TFA and CH$_2$Cl$_2$ (10 ml/10 ml) and stirred at RT. After 1.5 h at RT, TLC analysis indicated complete conversion of starting material. The solvent is removed by rotary evaporation, and replaced by dry DMF (5 ml). Under an atmosphere of argon, carbonyl diimidazole (236 mg, 1.46 mmol) is added. After 3 h at RT, TLC analysis indicated complete conversion of the carboxylic acid. An aqueous solution of ammonia (25%, 20 ml) is added at RT. After 15 minutes at RT, solvents are removed under high vacuum. The residue is dissolved in CH$_2$Cl$_2$/MeOH (9:1) and purified by FCC (CH$_2$Cl$_2$/MeOH, slow gradient from 90:10 to 40:60) to yield the title compound. $^1$H NMR (d$_6$-DMSO, 400 MHz): δ 2.69 (s, 3H), 2.93-3.18 (m, broad, 4H), 3.54 (s, 2H), 3.59-3.98 (m, broad, 4H), 6.95 (s, 1H), 7.02 (s, broad, 1H), 7.47 (s, broad, 1H), 8.45 (s, 1H). ES$^+$−MS: 303.2 [M+H]$^+$.

Preparation of [2-(4-Methyl-piperazin-1-yl)-5-trifluoromethyl-pyridin-4-yl]-acetic acid tert-butyl ester Sodium tert-butoxide (354 mg, 3.68 mmol) is dried under high vacuum at approximately 80° C. After purging with argon and cooling to RT, palladium acetate (60 mg, 0.27 mmol), rac-2,2'-bis-diphenylphosphanyl-[1,1]binaphthalenyl (rac-BINAP, 83 mg, 0.13 mmol) and (2-chloro-5-trifluoromethyl-pyridin-4-yl)-acetic acid tert-butyl ester (990 mg, 3.35 mmol) are added. The mixture is dissolved in dioxane (11 ml, degassed with three freeze-thaw cycles under HV/argon), and 1-methyl-piperazine (369 mg, 3.68 mmol) is added. The round bottom flask containing the reaction mixture is immersed into a pre-heated oil bath (T=85° C.). After 1 h, TLC analysis indicated almost complete conversion of starting materials. The reaction mixture is cooled to RT, diluted with EtOAc and poured into a saturated aqueous NH$_4$Cl solution. The organic layer is separated, washed with brine, dried over Na$_2$SO$_4$, and the solvent is evaporated. The residue is purified by FCC (CH$_2$Cl$_2$/MeOH, slow gradient from 99:1 to 94:6) to afford the title compound. $^1$H NMR (CDCl$_3$, 400 MHz): δ 1.44 (s, 9H), 2.34 (s, 3H), 2.50 (m, 4H), 3.59 (s, 2H), 3.66 (m, 4H), 6.54 (s, 1H), 8.35 (s, 1H). ES$^+$−MS: 360.3 [M+H]$^+$.

Preparation of (2-chloro-5-trifluoromethyl-pyridin-4-yl)-acetic acid tert-butyl ester Under an atmosphere of dry argon, a mixture of palladium dibenzylideneacetone (Pd$_2$(dba)$_3$, 22 mg, 0.02 mmol), di-tert-butylphosphino pentaphenylferrocene (17 mg, 0.02 mmol), 2-chloro-4-iodo-5-trifluoromethyl-pyridine (1.50 g, 4.88 mmol) and the Reformatzky reagent prepared from bromo-acetic acid tert-butyl ester and activated zinc metal (1.40 g, 5.37 mmol) is suspended in dry and degassed THF (20 ml). The mixture is heated to 60° C. After 45 minutes and after 90 minutes, additional batches of palladium dibenzylideneacetone (Pd$_2$(dba)$_3$, 22 mg, 0.02 mmol), di-tert-butylphosphino pentaphenylferrocene (17 mg, 0.02 mmol), and of the Reformatzky reagent (1.40 g, 5.37 mmol) are added. After a total of 2.5 h at 60° C., TLC analysis indicated complete conversion of starting materials. Upon cooling to RT, the reaction mixture is diluted with equal amounts of EtOAc and H$_2$O, and filtered through a tight plug of cotton. The organic layer is separated, washed with brine twice, dried over Na$_2$SO$_4$, and the solvent is evaporated. The residue is purified by FCC (hexanes/EtOAc, gradient from 100:0 to 97:3) to afford the title compound. $^1$H NMR (CDCl$_3$, 400 MHz): δ 1.44 (s, 9H), 3.71 (s, 2H), 7.39 (s, 1H), 8.63 (s, 1H). ES$^+$−MS: 294.1, 296.2 (Cl) [M+H]$^+$.

By following the procedure of Example 45, but using the appropriate starting materials, the compounds of formula I wherein R$_a$ and R$_b$ are as indicated in Table 10 below, may be obtained.

TABLE 10

I

| | R$_a$ | R$_b$ | MS |
|---|---|---|---|
| 46 | H | H | MH$^+$ 456 |

EXAMPLE 47

Gö 6976

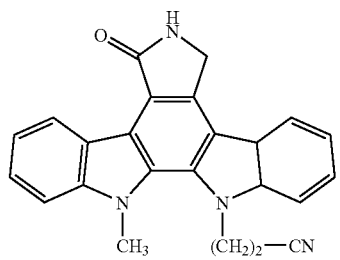

In accordance with the foregoing the present invention further provides:

1.1 A PKC inhibitor which possesses selectivity for α and β, and optionally θ, isoforms of PKC over one or more of the other isoforms of PKC, e.g. over one or more of the isoforms δ, ε and/or η, and which possesses selectivity for the PKC over one or more protein kinases which do not belong to the CDK family, e.g. over one or more tyrosine kinases, e.g. over one or more of PKA, PKB, Abl, Met, Src, Ins-R, Flt-3, JAK-2, KDR and Ret proteins, e.g. over one or more of Flt-3, JAK-2, KDR or Ret proteins, in free form or in a pharmaceutically acceptable salt form. The compound preferably shows a selectivity of at least 10 fold, more preferably 20 fold, most preferably 100 fold for α and β PKCs over one or more of the other PKC isoforms. The compound preferably shows a selectivity of at least 10 fold, more preferably 20 fold, most preferably 100 fold for PKC over the other protein kinases.

1.2 A PKC inhibitor which possesses selectivity for α and β, and optionally θ, isoforms of PKC over one or more of the other isoforms of PKC, e.g. over one or more of the isoforms δ, ε and/or η, and for which the ratio of the $IC_{50}$ value as determined by MLR assay to the $IC_{50}$ value as determined by BM assay is higher than 5, 10, 20, 30 or 50, in free form or in a pharmaceutically acceptable salt form. Preferably the ratio is higher than 20 or 30. Preferably the MLR and BM assays are done as defined hereinabove.

1.3 A PKC inhibitor which possesses selectivity for α, β and θ PKC isoforms over one or more of the other PKC isoforms, e.g. over one or more of the PKC isoforms δ, ε and/or η, in free form or in a pharmaceutically acceptable salt form. The compound may also possess selectivity for PKC over the other protein kinases, e.g. protein kinases which do not belong to the CDK family, e.g. over one or more tyrosine kinases. The compound preferably shows a selectivity for the PKC over the protein kinases which do not belong to the CDK family.

2.1 The use of a PKC inhibitor which is selective for α and β, and optionally θ, isoforms of PKC over one or more of the other isoforms of PKC, e.g. over one or more of the isoforms δ, ε and/or η, in free form or in a pharmaceutically acceptable salt form, for preventing or treating disorders or diseases mediated by T lymphocytes and/or PKC, or in the prevention, inhibition or control of acute or chronic graft rejection or graft versus host disease, in the prevention or treatment of autoimmune diseases or disorders, inflammatory diseases, infectious diseases, cardiovascular diseases or cancer.

2.2 The use of a PKC inhibitor for which the ratio of the $IC_{50}$ value as determined by MLR assay to the $IC_{50}$ value as determined by BM assay is higher than 5, 10, 20, 30 or 50, e.g. higher than 20 or 30, in free form or in a pharmaceutically acceptable salt form, for preventing or treating disorders or diseases mediated by T lymphocytes and/or PKC, or in the prevention, inhibition or control of acute or chronic graft rejection or graft versus host disease, in the prevention or treatment of autoimmune diseases or disorders, inflammatory diseases, infectious diseases, cardiovascular diseases, or cancer.

2.3 The use of a PKC inhibitor which is selective for PKC, optionally PKCα and PKCβ, over one or more other protein kinases, e.g. over one or more other protein kinases which do not belong to the CDK-family, e.g. over one or more tyrosine kinases, in free form or in a pharmaceutically acceptable salt form, for preventing or treating disorders or diseases mediated by T lymphocytes and/or PKC, or in the prevention, inhibition or control of acute or chronic graft rejection or graft versus host disease, in the prevention or treatment of autoimmune diseases or disorders, inflammatory diseases, infectious diseases, cardiovascular diseases, or cancer.

2.4 The use of a PKC inhibitor as indicated under 1.1, 1.2 or 1.3 above, e.g. a compound of formula I or Ib, or a pharmaceutically acceptable salt thereof, for preventing or treating disorders or diseases mediated by T lymphocytes and/or PKC, or in the prevention, inhibition or control of acute or chronic graft rejection or graft versus host disease, in the prevention or treatment of autoimmune diseases or disorders, inflammatory diseases, infectious diseases, cardiovascular diseases or cancer.

2.5 The use of a PKC inhibitor of the invention, e.g. as indicated under 1.1, 1.2 or 1.3 above, e.g. a compound of formula I or Ib, or a pharmaceutically acceptable salt thereof, in the inhibition of graft rejection or graft versus host disease.

2.6 The use of a PKC inhibitor of the invention, e.g. as indicated under 1.1, 1.2 or 1.3 above, e.g. a compound of formula I or Ib, or a pharmaceutically acceptable salt thereof, in the prevention or treatment of autoimmune diseases.

3. The use of a compound of formula I, or a pharmaceutically acceptable salt thereof, as a pharmaceutical.

4.1 The use of a compound of formula I, or a pharmaceutically acceptable salt thereof, as a selective PKC inhibitor, e.g. as a PKC inhibitor as indicated under 1.1, 1.2 or 1.3 above.

4.2 The use of a compound of formula Ib or a pharmaceutically acceptable salt thereof, as a selective PKC inhibitor as indicated under 1.1, 1.2 or 1.3 above.

5.1 A method for preventing or treating disorders or diseases mediated by T lymphocytes and/or PKC, in a subject in need of such a treatment, which method comprises administering to said subject an effective amount of a PKC inhibitor of the invention, e.g a PKC inhibitor which is selective for α and β, and optionally θ, isoforms of PKC over one or more of the other isoforms of PKC, e.g. over one or more of the isoforms δ, ε and η, or a PKC inhibitor as indicated under 1.1, 1.2 or 1.3 above, or a compound of formula I or Ib, or a pharmaceutically acceptable salt thereof.

5.2 A method for preventing or treating acute or chronic transplant rejection, graft versus host disease, inflammatory or autoimmune diseases, cancer, cardiovascular diseases or infectious diseases, in a subject in need of such a treatment, which method comprises administering to said subject an effective amount of a PKC inhibitor of the invention, e.g. a PKC inhibitor which is selective for α and β, and optionally θ, isoforms of PKC over one of more of the other isoforms of PKC, e.g. over one or more of the isoforms δ, ε and η, or a PKC inhibitor as indicated under 1.1, 1.2 or 1.3 above, or a compound of formula I or Ib, or a pharmaceutically acceptable salt thereof.

6.1 A pharmaceutical composition, e.g. for use in any of the methods as in 4.1 and 4.2 above comprising a PKC inhibitor of the invention, e.g. a PKC inhibitor which is selective for α and β, and optionally θ, isoforms of PKC over one or more of the other isoforms of PKC, e.g. over one or more of the isoforms δ, ε and η, or a PKC inhibitor as indicated under 1.1, 1.2 or 1.3 above, or a compound of formula I or Ib, in free form or pharmaceutically acceptable salt form, in association with a pharmaceutically acceptable diluent or carrier therefor.

6.2 A PKC inhibitor of the invention, e.g. a PKC inhibitor which is selective for the α and β, and optionally θ, isoforms of PKC over the other isoforms of PKC, e.g. over one or more of the isoforms δ, ε and η, or a PKC inhibitor as indicated under 1.1, 1.2 or 1.3 above, or a compound of formula I or Ib, in free form or pharmaceutically acceptable salt form, for use in the preparation of a pharmaceutical composition.

6.3 A PKC inhibitor of the invention, e.g. a PKC inhibitor which is selective for α and β, and optionally θ, isoforms of PKC over one or more of the other isoforms of PKC, e.g. over one or more of the isoforms δ, ε and η, or a PKC inhibitor as indicated under 1.1, 1.2 or 1.3 above, or a compound of formula I or Ib, in free form or pharmaceutically acceptable salt form, for use in the preparation of a pharmaceutical composition for use in any of the methods as in 5.1 and 5.2 above, e.g. in the inhibition of acute or chronic graft rejection or graft versus host disease, or in the prevention or treatment of autoimmune diseases or disorders.

For the use of the compounds of the invention, e.g. compounds of formula I or Ib, the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g. humans, is in the range from about 0.5 mg to about 2000 mg, conveniently administered, for example, in divided doses up to four times a day or in retard form.

The selective PKC inhibitors of the invention, e.g. compounds of formula I or Ib, may be administered by any conventional-route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a selective PKC inhibitors of the invention, e.g. a compound of formula I, in free form or in pharmaceutically acceptable salt form in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

Topical administration is e.g. to the skin. A further form of topical administration is to the eye.

The selective PKC inhibitors of the invention, e.g. compounds of formula I or Ib, may be administered in free form or in pharmaceutically acceptable salt form e.g. as indicated above. Such salts may be prepared in conventional manner and exhibit the same order of activity as the free compounds.

Assays

The assays used are described herein above.

The ratios of the $IC_{50}$ value for PKC $\beta$ to the $IC_{50}$ value for PKC$\alpha$, of the $IC_{50}$ value for PKC $\delta$ to the $IC_{50}$ value for PKC$\alpha$, of the $IC_{50}$ value for PKC $\delta$ to the $IC_{50}$ value for PKC$\alpha$, of the $IC_{50}$ value for PKC $\epsilon$ to the $IC_{50}$ value for PKC$\alpha$, of the $IC_{50}$ value for PKC $\eta$ to the $IC_{50}$ value for PKC$\alpha$, of the $IC_{50}$ value for PKC $\theta$ to the $IC_{50}$ value for PKC$\alpha$, of the $IC_{50}$ value as determined by the MLR assay and to the $IC_{50}$ value as determined by the BM assay, obtained for some compounds of the invention are indicated in table 11.

PKC$\alpha$, $\beta$, $\delta$, $\epsilon$, $\eta$ and $\theta$ assays, MLR and BM assays, are as described hereinabove.

TABLE 11

| Example | $\beta/\alpha$ | $\delta/\alpha$ | $\epsilon/\alpha$ | $\eta/\alpha$ | $\theta/\alpha$ | MLR/BM |
|---|---|---|---|---|---|---|
| 1 | 1.2 | 66.4 | 122.6 | 140.2 | 90.8 | 21.6 |
| 8 | 2.6 | 155.0 | 48.0 | 226.7 | 131.0 | 27.8 |
| 9 | 1.4 | 605.6 | 363.0 | 632.0 | 432.8 | 37.6 |
| 27 | 1.3 | 59.6 | 54.8 | 59.6 | 59.3 | 10.7 |
| 29 | 2.3 | 21.9 | 19.2 | 21.6 | 1.5 | 23.2 |
| 32 | 2.2 | 59.6 | 39.8 | 56.0 | 24.8 | 6.3 |
| 47 | 5.3 | 120.5 | 45.8 | 118.7 | 222.3 | 2.1 |

Selective inhibitor of the invention, e.g. selective inhibitors of the α, β, and optionally θ, PKC, in particular compounds of formula I or Ib, may be administered as the sole active ingredient or together with other drugs in immunomodulating regimens or other anti-inflammatory agents e.g. for the treatment or prevention of allo- or xenograft acute or chronic rejection or inflammatory or autoimmune disorders. For example, they may be used in combination with cyclosporines, or ascomycines or their immunosuppressive analogs or derivatives, e.g. cyclosporin A, ISA Tx247, FK-506, ABT-281, ASM 981; an mTOR inhibitor, e.g. rapamycin, 40-O-(2-hydroxyethyl)-rapamycin, CC1779, ABT578, or a rapalog, e.g. AP23573, AP23464, AP23675, AP23841, TAFA-93, biolimus 7 or biolimus 9 etc.; corticosteroids; cyclophosphamide; azathioprene; methotrexate; an S1P receptor modulator, e.g. FTY 720 or an analogue thereof; leflunomide or analogs thereof; mizoribine; mycophenolic acid or a salt thereof, e.g. sodium salt; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands; e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists. Selective PKC inhibitors of the invention, e.g. compounds of formula I, may also be administered together with an antiproliferative drug, e.g. a chemotherapeutic drug, e.g. as used in cancer treatment, including but not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide, or with an anti-diabetic drug, an insulin secretagogue or insulin secretion enhancer, e.g. a sulphonyl urea, e.g. tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide or tolylcyclamide, an oral insulinotropic agent derivative, e.g. a short acting insulin enhancer, e.g. meglitinide, repaglinide, a phenyl acetic acid derivative, e.g. nateglinide, a DPP IV inhibitor, e.g. 1-{2-[(5-cyanopyridin-2-yl)amino]ethylamino}acetyl-(2S)-cyano-pyrrolidine di-hydrochloride, LAF237, GLP-1 or a GLP-1 agonist analog, or an insulin sensitizer e.g. a peroxisome proliferator activated receptor γ agonist (PPARγ), e.g. a glitazone, a non-glitazone type such as a N-(2-benzoylphenyl)-L-tyrosine analogue, e.g. GI-262570, or an oxolidinedione, e.g. JTT501, a dual PPARγ/PPARα agonist, e.g. DRF-554158, NC-2100 or NN-622, a retinoid X receptor agonist or a rexinoid, e.g. 2-[1-(3,5,5,8,8-pentamethyl-5,6,7,8-tetrahydro-2-naphthyl)-cyclopropyl]-pyridine-5-carboxylic acid, 4-[(3,5,5,8,8-pentamethyl-5,6,7,8-tetrahydro-2-naphthyl)-2-carbonyl]-benzoic acid, 9-cis retinoic acid or an analog, derivative or a pharmaceutically acceptable salt thereof, in diabetes therapy, In accordance with the foregoing the present invention provides in a yet further aspect:

7. A method as defined above comprising co-administration, e.g. concomitantly or in sequence, of a therapeutically effective amount of a compound of the invention, e.g. a inhibitor selective for α, β, and optionally θ, PKCs over one or more of the other PKC isoforms, e.g. a inhibitor selective for PKC over one or more other protein kinases, e.g. over one or more protein kinases which do not belong to the CDK-1 family, e.g. a compound as indicated under 1.1, 1.2 and 1.3 above, e.g. a compound of formula I or Ib, in free form or in pharmaceutically acceptable salt form, and a second drug substance, said second drug substance being an immunosuppressant, immunomodulatory, anti-inflammatory, antiproliferative or anti-diabetic drug, e.g. as indicated above.

8. A therapeutic combination, e.g. a kit, comprising a) a compound of the invention, e.g. a inhibitor selective for α, β, and optionally θ, PKCs over one or more of the other PKC isoforms, e.g. a inhibitor selective for PKC over one or more other protein kinases, e.g. over one or more protein kinases which do not belong to the CDK-1 family, e.g. a compound as indicated under 1.1, 1.2 and 1.3 above, e.g. a compound of formula I or Ib, in free form or in pharmaceutically acceptable salt form, and b) at least one second agent selected from an immunosuppressant, immunomodulatory, anti-inflammatory, antiproliferative and anti-diabetic drug. Component a) and component b) may be used concomitantly or in sequence. The kit may comprise instructions for its administration.

Where a PKC selective inhibitor of the invention, e.g. a selective inhibitor of α, β, and optionally θ, PKCs, e.g. a compound of formula I or Ib, is administered in conjunction with other immunosuppressive/immunomodulatory, anti-inflammatory, antiproliferative or anti-diabetic therapy, e.g. for preventing or treating acute or chronic graft rejection or inflammatory or autoimmune disorders as hereinabove specified, dosages of the co-administered immunosuppressant, immunomodulatory, anti-inflammatory, antiproliferative or anti-diabetic compound will of course vary depending on the type of co-drug employed, e.g. whether it is a steroid or a cyclosporine, on the specific drug employed, on the condition being treated and so forth.

Selective PKC inhibitors of the invention, in particular inhibitors selective for α, β, and optionally θ, PKCs, over one or more other PKC isoforms, in particular compounds of formula I and Ib, have an interesting pharmacokinetic profile and interesting in vitro and in vivo activities.

The invention claimed is:

1. A compound of formula I

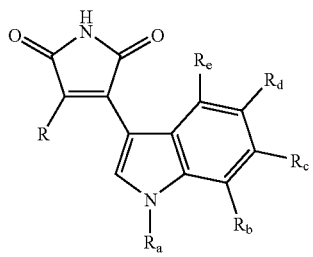

wherein $R_a$ is H; $C_{1-4}$alkyl; or $C_{1-4}$alkyl substituted by OH, $NH_2$, $NHC_{1-4}$alkyl or $N(di-C_{1-4}$alkyl$)_2$; one of $R_b$, $R_c$, $R_d$ and $R_e$ is halogen; $C_{1-4}$alkoxy; $C_{1-4}$alkyl; $CF_3$ or CN and the other three substituents are each H; or $R_b$, $R_c$, $R_d$ and $R_e$ are all H; and R is a radical of formula (a), (b) or (c)

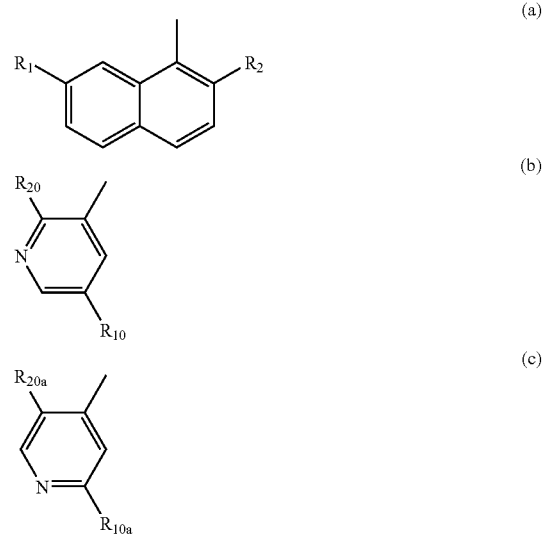

wherein
$R_1$ is $-(CH_2)_n-NR_3R_4$,
  wherein
  each of $R_3$ and $R_4$, independently, is H or $C_{1-4}$alkyl; or $R_3$ and $R_4$ form together with the nitrogen atom to which they are bound a heterocyclic residue;
  n is 0, 1 or 2; and
$R_2$ is H; halogen; $C_{1-4}$alkyl; $CF_3$; OH; SH; $NH_2$; $C_{1-4}$alkoxy; $C_{1-4}$alkylthio; $NHC_{1-4}$alkyl; $N(di-C_{1-4}$alkyl$)_2$, CN, alkyne or $NO_2$;
wherein
each of $R_{10}$ and $R_{10a}$, independently, is a heterocyclic residue; or a radical of formula α

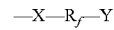 (α)

wherein S is a direct bond, O, S or $NR_{11}$ wherein $R_{11}$ is H or $C_{1-4}$alkyl,
$R_f$ is $C_{1-4}$alkylene or $C_{1-4}$alkylene wherein one $CH_2$ is replaced by $CR_xR_y$ wherein one of $R_x$ and $R_y$ is H and the other is $CH_3$, each of $R_x$ and $R_y$ is $CH_3$ or $R_x$ and $R_y$ form together $-CH_2-CH_2-$,
Y is bound to the terminal carbon atom and is selected from OH, $-NR_{30}R_{40}$ wherein each of $R_{30}$ and $R_{40}$, independently, is H, $C_{3-6}$cycloalkyl, $C_{3-6}$cycloalkyl-$C_{1-4}$alkyl, aryl-$C_{1-4}$alkyl, heteroaryl-$C_{1-4}$alkyl, $C_{2-6}$alkenyl or $C_{1-4}$alkyl optionally substituted on the terminal carbon atom by OH, halogen, $C_{1-4}$alkoxy or $-NR_{50}R_{60}$ wherein each of $R_{50}$ and $R_{60}$, independently, is H, $C_{1-4}$alkyl, $C_{3-6}$cycloalkyl, $C_{3-6}$cycloalkyl-$C_{1-4}$alkyl, aryl-$C_{1-4}$alkyl, or $R_{30}$ and $R_{40}$ form together with the nitrogen atom to which they are bound a heterocyclic residue; and
each of $R_{20}$ and $R_{20a}$, independently, is H; halogen; $C_{1-4}$alkyl; $C_{1-4}$alkoxy; $CF_3$; nitrile; nitro or amino;
or a salt thereof.

2. The compound according to claim 1, wherein $R_a$ is H or methyl; each of $R_2$, $R_{20}$ and $R_{20a}$, independently, is H, Cl, $NO_2$, F, $CF_3$ or methyl, n is 0 or 1; one of $R_b$, $R_c$, $R_d$ and $R_e$ is methyl or ethyl and the other three substituents are H; or $R_b$, $R_c$, $R_d$ and $R_e$ are all H; and each of $R_3$ and $R_4$, independently, is H, methyl, ethyl or i-propyl; or $R_3$ and $R_4$ form together with the nitrogen atom to which they are bound a heterocyclic residue optionally substituted; and each of $R_1$, $R_{10}$ and $R_{10a}$, independently, is a heterocyclic residue.

3. The compound according to claim 1, which is selected from

- 3-[5-Chloro-2-(4-methyl-piperazin-1-yl)-pyridin-4-yl]-4-(1H-indol-3-yl)-pyrrole-2,5-dione;
- 3-(2-Chloro-7-dimethylaminomethyl-naphthalen-1-yl)-4-(1-methyl-1H-indol-3-yl)-pyrrole-2,5-dione;
- 3-(7-Aminomethyl-2-Chloro-naphthalen-1-yl)-4-(1-methyl-1H-indol-3-yl)-pyrrole-2,5-dione;
- 3-(2-Chloro-7-methylaminomethyl-naphthalen-1-yl)-4-(1H-indol-3-yl)-pyrrole-2,5-dione;
- 3-(2-Chloro-7-methylaminomethyl-naphthalen-1-yl)-4-(1-methyl-1H-indol-3-yl)-pyrrole-2,5-dione;
- 3-(2-Chloro-7-methylaminomethyl-naphthalen-1-yl)-4-(7-methyl-1H-indol-3-yl)-pyrrole-2,5-dione;
- 3-(2-Chloro-7-methylaminomethyl-naphthalen-1-yl)-4-(6-methyl-1H-indol-3-yl)-pyrrole-2,5-dione;
- 3-(2-Chloro-7-methylaminomethyl-naphthalen-1-yl)-4-(5-methyl-1H-indol-3-yl)-pyrrole-2,5-dione;
- 3-(2-Chloro-7-dimethylaminomethyl-naphthalen-1-yl)-4-(7-methyl-1H-indol-3-yl)-pyrrole-2,5-dione;
- 3-(2-Chloro-7-dimethylaminomethyl-naphthalen-1-yl)-4-(1H-indol-3-yl)-pyrrole-2,5-dione;
- 3-(2-Chloro-7-dimethylaminomethyl-naphthalen-1-yl)-4-(6-methyl-1H-indol-3-yl)-pyrrole-2,5-dione;
- 3-(2-Chloro-7-dimethylaminomethyl-naphthalen-1-yl)-4-(5-methyl-1H-indol-3-yl)-pyrrole-2,5-dione;
- 3-{2-Chloro-7-[(ethyl-methyl-amino)-methyl]-naphthalen-1-yl}-4-(1-methyl-1H-indol-3-yl)-pyrrole-2,5-dione;
- 3-(2-Chloro-7-diethylaminomethyl-naphthalen-1-yl)-4-(1-methyl-1H-indol-3-yl)-pyrrole-2,5-dione;
- 3-(2-Chloro-7-ethylaminomethyl-naphthalen-1-yl)-4-(1-methyl-1H-indol-3-yl)-pyrrole-2,5-dione;
- 3-[2-Chloro-7-(isopropylamino-methyl)-naphthalen-1-yl]-4-(1-methyl-1H-indol-3-yl)-pyrrole-2,5-dione;
- 3-[2-Chloro-7-(4-methyl-piperazin-1-ylmethyl)-naphthalen-1-yl]-4-(1-methyl-1H-indol-3-yl)-pyrrole-2,5-dione;
- 3-(2-Chloro-7-pyrrolidin-1-ylmethyl-naphthalen-1-yl)-4-(1-methyl-1H-indol-3-yl)-pyrrole-2,5-dione;
- 3-(7-Aminomethyl-2-methyl-naphthalen-1-yl)-4-(1,7-dimethyl-1H-indol-3-yl)-pyrrole-2,5-dione;
- 3-(7-Aminomethyl-2-methyl-naphthalen-1-yl)-4-(7-methyl-1H-indol-3-yl)-pyrrole-2,5-dione;
- 3-(7-Aminomethyl-2-methyl-naphthalen-1-yl)-4-(1H-indol-3-yl)-pyrrole-2,5-dione;
- 3-(7-Aminomethyl-2-methyl-naphthalen-1-yl)-4-(1-methyl-1H-indol-3-yl)-pyrrole-2,5-dione;
- 3-(7-Aminomethyl-naphthalen-1-yl)-4-(1H-indol-3-yl)-pyrrole-2,5-dione;
- 3-(7-Aminomethyl-naphthalen-1-yl)-4-(1-methyl-1H-indol-3-yl)-pyrrole-2,5-dione;
- 3-(7-Amino-naphthalen-1-yl)-4-(1-methyl-1H-indol-3-yl)-pyrrole-2,5-dione;
- 3-(7-Amino-naphthalen-1-yl)-4-(1H-indol-3-yl)-pyrrole-2,5-dione;
- 3-(7-Dimethylaminomethyl-2-fluoro-naphthalen-1-yl)-4-(7-methyl-1H-indol-3-yl)-pyrrole-2,5-dione;
- 3-(7-dimethylaminomethyl-2-fluoro-naphthalen-1-yl)-4-(1H-indol-3-yl)-pyrrole-2,5-dione;
- 3-(1-Methyl-1H-indol-3-yl)-4-[5-(4-methyl-piperazin-1-yl)-pyridin-3-yl]-pyrrole-2,5-dione;
- 3-(1H-indol-3-yl)-4-[5-(4-methyl-piperazin-1-yl)-pyridin-3-yl]-pyrrole-2,5-dione;
- 3-(7-methyl-1H-indol-3-yl)-4-[5-(4-methyl-piperazin-1-yl)-2-trifluoromethyl-pyridin-3-yl]-pyrrole-2,5-dione;
- 3-(1H-indol-3-yl)-4-[5-(4-methyl-piperazin-1-yl)-2-trifluoromethyl-pyridin-3-yl]-pyrrole-2,5-dione;
- 3-(1-methyl-1H-indol-3-yl)-4-[5-(4-methyl-piperazin-1-yl)-2-trifluoromethyl-pyridin-3-yl]-pyrrole-2,5-dione;
- 3-(7-methyl-1H-indol-3-yl)-4-[5-(4-methyl-piperazin-1-yl)-pyridin-3-yl]-pyrrole-2,5-dione;
- 3-(1H-indol-3-yl)-4-[5-(4-methyl-piperazin-1-yl)-2-nitro-pyridin-3-yl]-pyrrole-2,5-dione;
- 3-[2-chloro-5-(4-methyl-piperazin-1-yl)-pyridin-3-yl]-4-(7-methyl-1H-indol-3-yl)-pyrrole-2,5-dione;
- 3-(1H-indol-3-yl)-4-[5-methyl-2-(4-methyl-piperazin-1-yl)-pyridin-4-yl]-pyrrole-2,5-dione;
- 3-(1H-indol-3-yl)-4-[2-(4-methyl-piperazin-1-yl)-5-nitro-pyridin-4-yl]-pyrrole-2,5-dione; and
- 3-(1H-indol-3-yl)-4-[2-(4-methyl-piperazin-1-yl)-5-trifluoromethyl-pyridin-4-yl]-pyrrole-2,5-dione;

in free form or in a pharmaceutically acceptable salt form.

4. The compound according to claim 1, in free form or in a pharmaceutically acceptable salt form, for use as a pharmaceutical.

5. A process for the production of the compound according to claim 1, wherein the process comprises reacting a compound of formula II

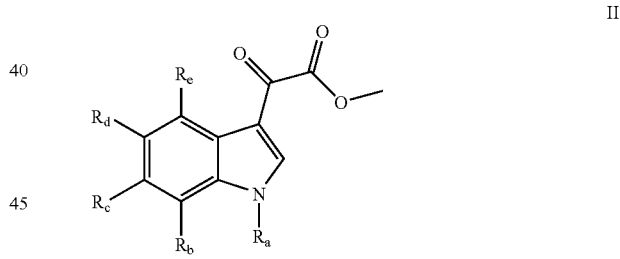

wherein $R_a$ to $R_e$ are as defined in claim 1,
with a compound of formula III

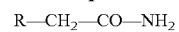
(III)

wherein R is as defined in claim 1,
and, where required, converting the resulting compound of formula I obtained in free form to a salt form or vice versa, as appropriate.

* * * * *